(12) United States Patent
Knopf et al.

(10) Patent No.: US 7,456,149 B2
(45) Date of Patent: Nov. 25, 2008

(54) ALK7 AND MYOSTATIN INHIBITORS AND USES THEREOF

(75) Inventors: John Knopf, Carlisle, MA (US); Jasbir Seehra, Lexington, MA (US)

(73) Assignee: Acceleron Pharma, Inc., Cambridge, MA (US)

(*) Notice: Subject to any disclaimer, the term of this patent is extended or adjusted under 35 U.S.C. 154(b) by 281 days.

(21) Appl. No.: 11/071,686

(22) Filed: Mar. 2, 2005

(65) Prior Publication Data
US 2006/0030522 A1 Feb. 9, 2006

Related U.S. Application Data

(60) Provisional application No. 60/549,352, filed on Mar. 2, 2004.

(51) Int. Cl.
*A61K 38/16* (2006.01)
*C12N 15/11* (2006.01)
*C12N 15/13* (2006.01)

(52) U.S. Cl. .................. 514/2; 514/12; 424/133.1; 424/178.1; 435/69.7

(58) Field of Classification Search ............ None
See application file for complete search history.

(56) References Cited

U.S. PATENT DOCUMENTS

| | | | |
|---|---|---|---|
| 5,538,892 A | 7/1996 | Donahoe et al. | |
| 5,614,609 A | 3/1997 | Ibanez et al. | |
| 5,789,565 A | 8/1998 | Ibanez et al. | |
| 5,811,245 A | 9/1998 | Ibanez et al. | |
| 5,891,638 A | 4/1999 | Ibanez et al. | |
| 5,976,815 A | 11/1999 | Ibanez et al. | |
| 6,162,896 A * | 12/2000 | Mathews et al. | 530/350 |
| 6,368,597 B1 * | 4/2002 | Strassmann et al. | 424/158.1 |
| 6,818,440 B2 | 11/2004 | Plowman et al. | |
| 2004/0219139 A1 | 11/2004 | Plowman et al. | |
| 2004/0234540 A1 | 11/2004 | Plowman et al. | |
| 2005/0026184 A1 | 2/2005 | Plowman et al. | |

FOREIGN PATENT DOCUMENTS

| | | |
|---|---|---|
| JP | 2003113111 A | 4/2003 |
| WO | WO-96/12805 | 5/1996 |
| WO | WO 98/49317 | 11/1998 |
| WO | WO 02/085306 A2 | 10/2002 |
| WO | WO 03/027248 A2 | 4/2003 |
| WO | WO 03/072714 A2 | 9/2003 |
| WO | WO 2004/108157 A2 | 12/2004 |

OTHER PUBLICATIONS

Whittemore et al., Jan. 2003, Biochemical and Biophysical Research Communications 300:965-971.*
Massague, 1998, Annu. Rev. Biochem. 67:753-791.*
Kirsch et al., 2000, Nature Structural Biology 7:492-496.*
Bondstam, et al., "cDNA Cloning, Expression Studies and Chromosome Mapping of Human Type I Serine/Threonine Kinase Receptor ALK7 (ACVR1C)," Cytogenetics and Cell Genetics, 95(3-3:157-162 (2001).
Reissmann, et al., "The Orphan Receptor ALK7 and the Activin Receptor ALK4 Mediate Signaling by Nodal Proteins During Vertebrate Development," Genes & Development, 15(15):2010-2022 (2001).
Roberts, et al., "Identification of Novel Isoforms of Activin Receptor-Like Kinase 7 (ALK7) Generated by Alternative Splicing and Expression of ALK7 and Its Ligand, Nodal, in Human Placenta," The Society for the Study of Reproduction, Inc. 68(5):1719-1726 (2003).
Ryden, et al., "A Novel Type I Receptor Serine-Threonine Kinase Predominantly Expressed in the Adult Central Nervous System," The Journal of Biological Chemistry, 271(48): 30603-30609 (1996).
Tsuchida, et al., "Activin Isoforms Signal Through Type I Receptor Serine/Threonine Kinase ALK7," Molecular and Cellular Endocrinology 220:59-65 (2004).
Tsuchida, et al., "Molecular Cloning of a Novel Type I Receptor Serine/Threonine Kinase for the TGF β Superfamily from Rat Brain," Department of Molecular Genetics 7(6):467-478 (1996).
Greenwald, et. al., "The BMP7/ActRII Extracellular Domain Comples Provides New Insights into the Cooperative Nature of Receptor Assembly," Molecular Cell, 11, 605-617 (2003).

* cited by examiner

*Primary Examiner*—Elizabeth C. Kemmerer
(74) *Attorney, Agent, or Firm*—Ropes & Gray LLP

(57) ABSTRACT

The invention relates to ALK7 soluble receptors and their uses as antagonists of the function of certain ligands such as GDF-8 (Myostatin) and GDF-11. The ALK7 soluble receptor of the invention is useful as antagonists of GDF-8 and GDF-11 in the treatment of neuronal diseases or conditions such as stroke, spinal cord injury, and all peripheral nerve diseases. The ALK7 soluble receptor of the invention is also useful as GH (growth hormone) equivalent, and for increasing muscle mass.

4 Claims, 4 Drawing Sheets

SEQUENCE LISTING

<160> NUMBER OF SEQ ID NOS: 7

<210> SEQ ID NO 1
<211> LENGTH: 1482
<212> TYPE: DNA
<213> ORGANISM: Homo sapiens
<220> FEATURE:
<221> NAME/KEY: CDS
<222> LOCATION: (1)...(1482)

<400> SEQUENCE: 1

```
atg acc cgg gcg ctc tgc tca gcg ctc cgc cag gct ctc ctg ctg ctc      48
Met Thr Arg Ala Leu Cys Ser Ala Leu Arg Gln Ala Leu Leu Leu Leu
 1               5                  10                  15 gca gcg gcc gcc gag ctc tcg cca gga ctg aag tgt gta tgt ctt ttg      96
Ala Ala Ala Ala Glu Leu Ser Pro Gly Leu Lys Cys Val Cys Leu Leu
             20                  25                  30 tgt gat tct tca aac ttt acc tgc caa aca gaa gga gca tgt tgg gca     144
Cys Asp Ser Ser Asn Phe Thr Cys Gln Thr Glu Gly Ala Cys Trp Ala
         35                  40                  45 tca gtc atg cta acc aat gga aaa gag cag gtg atc aaa tcc tgt gtc     192
Ser Val Met Leu Thr Asn Gly Lys Glu Gln Val Ile Lys Ser Cys Val
     50                  55                  60 tcc ctt cca gaa ctg aat gct caa gtc ttc tgt cat agt tcc aac aat     240
Ser Leu Pro Glu Leu Asn Ala Gln Val Phe Cys His Ser Ser Asn Asn
 65                  70                  75                  80 gtt acc aaa acc gaa tgc tgc ttc aca gat ttt tgc aac aac ata aca     288
Val Thr Lys Thr Glu Cys Cys Phe Thr Asp Phe Cys Asn Asn Ile Thr
                 85                  90                  95 ctg cac ctt cca aca gca tca cca aat gcc cca aaa ctt gga ccc atg     336
Leu His Leu Pro Thr Ala Ser Pro Asn Ala Pro Lys Leu Gly Pro Met
            100                 105                 110 gag ctg gcc atc att att act gtg cct gtt tgc ctc ctg tcc ata gct     384
Glu Leu Ala Ile Ile Ile Thr Val Pro Val Cys Leu Leu Ser Ile Ala
        115                 120                 125 gcg atg ctg aca gta tgg gca tgc cag ggt cga cag tgc tcc tac agg     432
Ala Met Leu Thr Val Trp Ala Cys Gln Gly Arg Gln Cys Ser Tyr Arg
    130                 135                 140 aag aaa aag aga cca aat gtg gag gaa cca ctc tct gag tgc aat ctg     480
Lys Lys Lys Arg Pro Asn Val Glu Glu Pro Leu Ser Glu Cys Asn Leu
145                 150                 155                 160 gta aat gct gga aaa act ctg aaa gat ctg att tat gat gtg acc gcc     528
Val Asn Ala Gly Lys Thr Leu Lys Asp Leu Ile Tyr Asp Val Thr Ala
                165                 170                 175 tct gga tct ggc tct ggt cta cct ctg ttg gtt caa agg aca att gca     576
Ser Gly Ser Gly Ser Gly Leu Pro Leu Leu Val Gln Arg Thr Ile Ala
            180                 185                 190 agg acg att gtg ctt cag gaa ata gta gga aaa ggt aga ttt ggt gag     624
Arg Thr Ile Val Leu Gln Glu Ile Val Gly Lys Gly Arg Phe Gly Glu
        195                 200                 205 gtg tgg cat gga aga tgg tgt ggg gaa gat gtg gct gtg aaa ata ttc     672
Val Trp His Gly Arg Trp Cys Gly Glu Asp Val Ala Val Lys Ile Phe
    210                 215                 220 tcc tcc aga gat gaa aga tct tgg ttt cgt gag gca gaa att tac cag     720
Ser Ser Arg Asp Glu Arg Ser Trp Phe Arg Glu Ala Glu Ile Tyr Gln
225                 230                 235                 240 acg gtc atg ctg cga cat gaa aac atc ctt ggt ttc att gct gct gac     768
Thr Val Met Leu Arg His Glu Asn Ile Leu Gly Phe Ile Ala Ala Asp
                245                 250                 255
```

```
aac aaa gat aat gga act tgg act caa ctt tgg ctg gta tct gaa tat    816
Asn Lys Asp Asn Gly Thr Trp Thr Gln Leu Trp Leu Val Ser Glu Tyr
        260                 265                 270 cat gaa cag ggc tcc tta tat gac tat ttg aat aga aat ata gtg acc    864
His Glu Gln Gly Ser Leu Tyr Asp Tyr Leu Asn Arg Asn Ile Val Thr
    275                 280                 285 gtg gct gga atg atc aag ctg gcg ctc tca att gct agt ggt ctg gca    912
Val Ala Gly Met Ile Lys Leu Ala Leu Ser Ile Ala Ser Gly Leu Ala
290                 295                 300 cac ctt cat atg gag att gtt ggt aca caa ggt aaa cct gct att gct    960
His Leu His Met Glu Ile Val Gly Thr Gln Gly Lys Pro Ala Ile Ala
305                 310                 315                 320 cat cga gac ata aaa tca aag aat atc tta gtg aaa aag tgt gaa act   1008
His Arg Asp Ile Lys Ser Lys Asn Ile Leu Val Lys Lys Cys Glu Thr
            325                 330                 335 tgt gcc ata gcg gac tta ggg ttg gct gtg aag cat gat tca ata ctg   1056
Cys Ala Ile Ala Asp Leu Gly Leu Ala Val Lys His Asp Ser Ile Leu
        340                 345                 350 aac act atc gac ata cct cag aat cct aaa gtg gga acc aag agg tat   1104
Asn Thr Ile Asp Ile Pro Gln Asn Pro Lys Val Gly Thr Lys Arg Tyr
    355                 360                 365 atg gct cct gaa atg ctt gat gat aca atg aat gtg aat atc ttt gag   1152
Met Ala Pro Glu Met Leu Asp Asp Thr Met Asn Val Asn Ile Phe Glu
370                 375                 380 tcc ttc aaa cga gct gac atc tat tct gtt ggt ctg gtt tac tgg gaa   1200
Ser Phe Lys Arg Ala Asp Ile Tyr Ser Val Gly Leu Val Tyr Trp Glu
385                 390                 395                 400 ata gcc cgg agg tgt tca gtc gga gga att gtt gag gag tac caa ttg   1248
Ile Ala Arg Arg Cys Ser Val Gly Gly Ile Val Glu Glu Tyr Gln Leu
            405                 410                 415 cct tat tat gac atg gtg cct tca gat ccc tcg ata gag gaa atg aga   1296
Pro Tyr Tyr Asp Met Val Pro Ser Asp Pro Ser Ile Glu Glu Met Arg
        420                 425                 430 aag gtt gtt tgt gac cag aag ttt cga cca agt atc cca aac cag tgg   1344
Lys Val Val Cys Asp Gln Lys Phe Arg Pro Ser Ile Pro Asn Gln Trp
    435                 440                 445 caa agt tgt gaa gca ctc cga gtc atg ggg aga ata atg cgt gag tgt   1392
Gln Ser Cys Glu Ala Leu Arg Val Met Gly Arg Ile Met Arg Glu Cys
450                 455                 460 tgg tat gcc aac gga gcg gcc cgc cta act gct ctt cgt att aag aag   1440
Trp Tyr Ala Asn Gly Ala Ala Arg Leu Thr Ala Leu Arg Ile Lys Lys
465                 470                 475                 480 act ata tct caa ctt tgt gtc aaa gaa gac tgc aaa gcc taa            1482
Thr Ile Ser Gln Leu Cys Val Lys Glu Asp Cys Lys Ala *
            485                 490
```

<210> SEQ ID NO 2
<211> LENGTH: 493
<212> TYPE: PRT
<213> ORGANISM: Homo sapiens

<400> SEQUENCE: 2

```
Met Thr Arg Ala Leu Cys Ser Ala Leu Arg Gln Ala Leu Leu Leu Leu
 1               5                  10                  15

Ala Ala Ala Ala Glu Leu Ser Pro Gly Leu Lys Cys Val Cys Leu Leu
                20                  25                  30

Cys Asp Ser Ser Asn Phe Thr Cys Gln Thr Glu Gly Ala Cys Trp Ala
            35                  40                  45

Ser Val Met Leu Thr Asn Gly Lys Glu Gln Val Ile Lys Ser Cys Val
        50                  55                  60
```

-continued

```
Ser Leu Pro Glu Leu Asn Ala Gln Val Phe Cys His Ser Asn Asn
 65                  70                  75                  80

Val Thr Lys Thr Glu Cys Cys Phe Thr Asp Phe Cys Asn Asn Ile Thr
                     85                  90                  95

Leu His Leu Pro Thr Ala Ser Pro Asn Ala Pro Lys Leu Gly Pro Met
                100                 105                 110

Glu Leu Ala Ile Ile Ile Thr Val Pro Val Cys Leu Leu Ser Ile Ala
                115                 120                 125

Ala Met Leu Thr Val Trp Ala Cys Gln Gly Arg Gln Cys Ser Tyr Arg
        130                 135                 140

Lys Lys Lys Arg Pro Asn Val Glu Glu Pro Leu Ser Glu Cys Asn Leu
145                 150                 155                 160

Val Asn Ala Gly Lys Thr Leu Lys Asp Leu Ile Tyr Asp Val Thr Ala
                165                 170                 175

Ser Gly Ser Gly Ser Gly Leu Pro Leu Leu Val Gln Arg Thr Ile Ala
                180                 185                 190

Arg Thr Ile Val Leu Gln Glu Ile Val Gly Lys Gly Arg Phe Gly Glu
        195                 200                 205

Val Trp His Gly Arg Trp Cys Gly Glu Asp Val Ala Val Lys Ile Phe
        210                 215                 220

Ser Ser Arg Asp Glu Arg Ser Trp Phe Arg Glu Ala Glu Ile Tyr Gln
225                 230                 235                 240

Thr Val Met Leu Arg His Glu Asn Ile Leu Gly Phe Ile Ala Ala Asp
                245                 250                 255

Asn Lys Asp Asn Gly Thr Trp Thr Gln Leu Trp Leu Val Ser Glu Tyr
                260                 265                 270

His Glu Gln Gly Ser Leu Tyr Asp Tyr Leu Asn Arg Asn Ile Val Thr
        275                 280                 285

Val Ala Gly Met Ile Lys Leu Ala Leu Ser Ile Ala Ser Gly Leu Ala
        290                 295                 300

His Leu His Met Glu Ile Val Gly Thr Gln Gly Lys Pro Ala Ile Ala
305                 310                 315                 320

His Arg Asp Ile Lys Ser Lys Asn Ile Leu Val Lys Lys Cys Glu Thr
                325                 330                 335

Cys Ala Ile Ala Asp Leu Gly Leu Ala Val Lys His Asp Ser Ile Leu
                340                 345                 350

Asn Thr Ile Asp Ile Pro Gln Asn Pro Lys Val Gly Thr Lys Arg Tyr
        355                 360                 365

Met Ala Pro Glu Met Leu Asp Asp Thr Met Asn Val Asn Ile Phe Glu
        370                 375                 380

Ser Phe Lys Arg Ala Asp Ile Tyr Ser Val Gly Leu Val Tyr Trp Glu
385                 390                 395                 400

Ile Ala Arg Arg Cys Ser Val Gly Gly Ile Val Glu Glu Tyr Gln Leu
                405                 410                 415

Pro Tyr Tyr Asp Met Val Pro Ser Asp Pro Ser Ile Glu Glu Met Arg
                420                 425                 430

Lys Val Val Cys Asp Gln Lys Phe Arg Pro Ser Ile Pro Asn Gln Trp
        435                 440                 445

Gln Ser Cys Glu Ala Leu Arg Val Met Gly Arg Ile Met Arg Glu Cys
        450                 455                 460

Trp Tyr Ala Asn Gly Ala Ala Arg Leu Thr Ala Leu Arg Ile Lys Lys
465                 470                 475                 480

Thr Ile Ser Gln Leu Cys Val Lys Glu Asp Cys Lys Ala
```

<210> SEQ ID NO 3
<211> LENGTH: 1242
<212> TYPE: DNA
<213> ORGANISM: Homo sapiens
<220> FEATURE:
<221> NAME/KEY: CDS
<222> LOCATION: (1)...(1242)

<400> SEQUENCE: 3

| | | | | | | | | | | | | | | | | |
|---|---|---|---|---|---|---|---|---|---|---|---|---|---|---|---|---|
| atg | acc | cgg | gcg | ctc | tgc | tca | gcg | ctc | cgc | cag | gct | ctc | ctg | ctg | ctc | 48 |
| Met | Thr | Arg | Ala | Leu | Cys | Ser | Ala | Leu | Arg | Gln | Ala | Leu | Leu | Leu | Leu | |
| 1 | | | | 5 | | | | | 10 | | | | | 15 | | |
| gca | gcg | gcc | gcc | gag | ctc | tcg | cca | gga | ctg | aag | tgt | gta | tgt | ctt | ttg | 96 |
| Ala | Ala | Ala | Ala | Glu | Leu | Ser | Pro | Gly | Leu | Lys | Cys | Val | Cys | Leu | Leu | |
| | | | 20 | | | | | 25 | | | | | 30 | | | |
| tgt | gat | tct | tca | aac | ttt | acc | tgc | caa | aca | gaa | gga | gca | tgt | tgg | gca | 144 |
| Cys | Asp | Ser | Ser | Asn | Phe | Thr | Cys | Gln | Thr | Glu | Gly | Ala | Cys | Trp | Ala | |
| | | 35 | | | | | 40 | | | | | 45 | | | | |
| tca | gtc | atg | cta | acc | aat | gga | aaa | gag | cag | gtg | atc | aaa | tcc | tgt | gtc | 192 |
| Ser | Val | Met | Leu | Thr | Asn | Gly | Lys | Glu | Gln | Val | Ile | Lys | Ser | Cys | Val | |
| | 50 | | | | | 55 | | | | | 60 | | | | | |
| tcc | ctt | cca | gaa | ctg | aat | gct | caa | gtc | ttc | tgt | cat | agt | tcc | aac | aat | 240 |
| Ser | Leu | Pro | Glu | Leu | Asn | Ala | Gln | Val | Phe | Cys | His | Ser | Ser | Asn | Asn | |
| 65 | | | | | 70 | | | | | 75 | | | | | 80 | |
| gtt | acc | aaa | acc | gaa | tgc | tgc | ttc | aca | gat | ttt | tgc | aac | aac | ata | aca | 288 |
| Val | Thr | Lys | Thr | Glu | Cys | Cys | Phe | Thr | Asp | Phe | Cys | Asn | Asn | Ile | Thr | |
| | | | | 85 | | | | | 90 | | | | | 95 | | |
| ctg | cac | ctt | cca | aca | ggt | cta | cct | ctg | ttg | gtt | caa | agg | aca | att | gca | 336 |
| Leu | His | Leu | Pro | Thr | Gly | Leu | Pro | Leu | Leu | Val | Gln | Arg | Thr | Ile | Ala | |
| | | | 100 | | | | | 105 | | | | | 110 | | | |
| agg | acg | att | gtg | ctt | cag | gaa | ata | gta | gga | aaa | ggt | aga | ttt | ggt | gag | 384 |
| Arg | Thr | Ile | Val | Leu | Gln | Glu | Ile | Val | Gly | Lys | Gly | Arg | Phe | Gly | Glu | |
| | | 115 | | | | | 120 | | | | | 125 | | | | |
| gtg | tgg | cat | gga | aga | tgg | tgt | ggg | gaa | gat | gtg | gct | gtg | aaa | ata | ttc | 432 |
| Val | Trp | His | Gly | Arg | Trp | Cys | Gly | Glu | Asp | Val | Ala | Val | Lys | Ile | Phe | |
| | 130 | | | | | 135 | | | | | 140 | | | | | |
| tcc | tcc | aga | gat | gaa | aga | tct | tgg | ttt | cgt | gag | gca | gaa | att | tac | cag | 480 |
| Ser | Ser | Arg | Asp | Glu | Arg | Ser | Trp | Phe | Arg | Glu | Ala | Glu | Ile | Tyr | Gln | |
| 145 | | | | | 150 | | | | | 155 | | | | | 160 | |
| acg | gtc | atg | ctg | cga | cat | gaa | aac | atc | ctt | ggt | ttc | att | gct | gct | gac | 528 |
| Thr | Val | Met | Leu | Arg | His | Glu | Asn | Ile | Leu | Gly | Phe | Ile | Ala | Ala | Asp | |
| | | | | 165 | | | | | 170 | | | | | 175 | | |
| aac | aaa | gat | aat | gga | act | tgg | act | caa | ctt | tgg | ctg | gta | tct | gaa | tat | 576 |
| Asn | Lys | Asp | Asn | Gly | Thr | Trp | Thr | Gln | Leu | Trp | Leu | Val | Ser | Glu | Tyr | |
| | | | 180 | | | | | 185 | | | | | 190 | | | |
| cat | gaa | cag | ggc | tcc | tta | tat | gac | tat | ttg | aat | aga | aat | ata | gtg | acc | 624 |
| His | Glu | Gln | Gly | Ser | Leu | Tyr | Asp | Tyr | Leu | Asn | Arg | Asn | Ile | Val | Thr | |
| | | 195 | | | | | 200 | | | | | 205 | | | | |
| gtg | gct | gga | atg | atc | aag | ctg | gcg | ctc | tca | att | gct | agt | ggt | ctg | gca | 672 |
| Val | Ala | Gly | Met | Ile | Lys | Leu | Ala | Leu | Ser | Ile | Ala | Ser | Gly | Leu | Ala | |
| | 210 | | | | | 215 | | | | | 220 | | | | | |
| cac | ctt | cat | atg | gag | att | gtt | ggt | aca | caa | ggt | aaa | cct | gct | att | gct | 720 |
| His | Leu | His | Met | Glu | Ile | Val | Gly | Thr | Gln | Gly | Lys | Pro | Ala | Ile | Ala | |
| 225 | | | | | 230 | | | | | 235 | | | | | 240 | |
| cat | cga | gac | ata | aaa | tca | aag | aat | atc | tta | gtg | aaa | aag | tgt | gaa | act | 768 |
| His | Arg | Asp | Ile | Lys | Ser | Lys | Asn | Ile | Leu | Val | Lys | Lys | Cys | Glu | Thr | |
| | | | | 245 | | | | | 250 | | | | | 255 | | |
| tgt | gcc | ata | gcg | gac | tta | ggg | ttg | gct | gtg | aag | cat | gat | tca | ata | ctg | 816 |
| Cys | Ala | Ile | Ala | Asp | Leu | Gly | Leu | Ala | Val | Lys | His | Asp | Ser | Ile | Leu | |

-continued

```
                260                 265                 270
aac act atc gac ata cct cag aat cct aaa gtg gga acc aag agg tat     864
Asn Thr Ile Asp Ile Pro Gln Asn Pro Lys Val Gly Thr Lys Arg Tyr
        275                 280                 285 atg gct cct gaa atg ctt gat gat aca atg aat gtg aat atc ttt gag     912
Met Ala Pro Glu Met Leu Asp Asp Thr Met Asn Val Asn Ile Phe Glu
    290                 295                 300 tcc ttc aaa cga gct gac atc tat tct gtt ggt ctg gtt tac tgg gaa     960
Ser Phe Lys Arg Ala Asp Ile Tyr Ser Val Gly Leu Val Tyr Trp Glu
305                 310                 315                 320 ata gcc cgg agg tgt tca gtc gga gga att gtt gag gag tac caa ttg    1008
Ile Ala Arg Arg Cys Ser Val Gly Gly Ile Val Glu Glu Tyr Gln Leu
                325                 330                 335 cct tat tat gac atg gtg cct tca gat ccc tcg ata gag gaa atg aga    1056
Pro Tyr Tyr Asp Met Val Pro Ser Asp Pro Ser Ile Glu Glu Met Arg
        340                 345                 350 aag gtt gtt tgt gac cag aag ttt cga cca agt atc cca aac cag tgg    1104
Lys Val Val Cys Asp Gln Lys Phe Arg Pro Ser Ile Pro Asn Gln Trp
    355                 360                 365 caa agt tgt gaa gca ctc cga gtc atg ggg aga ata atg cgt gag tgt    1152
Gln Ser Cys Glu Ala Leu Arg Val Met Gly Arg Ile Met Arg Glu Cys
370                 375                 380 tgg tat gcc aac gga gcg gcc cgc cta act gct ctt cgt att aag aag    1200
Trp Tyr Ala Asn Gly Ala Ala Arg Leu Thr Ala Leu Arg Ile Lys Lys
385                 390                 395                 400 act ata tct caa ctt tgt gtc aaa gaa gac tgc aaa gcc taa            1242
Thr Ile Ser Gln Leu Cys Val Lys Glu Asp Cys Lys Ala *
                405                 410
```

<210> SEQ ID NO 4
<211> LENGTH: 413
<212> TYPE: PRT
<213> ORGANISM: Homo sapiens

<400> SEQUENCE: 4

```
Met Thr Arg Ala Leu Cys Ser Ala Leu Arg Gln Ala Leu Leu Leu Leu
1               5                   10                  15

Ala Ala Ala Glu Leu Ser Pro Gly Leu Lys Cys Val Cys Leu Leu
                20                  25                  30

Cys Asp Ser Ser Asn Phe Thr Cys Gln Thr Glu Gly Ala Cys Trp Ala
            35                  40                  45

Ser Val Met Leu Thr Asn Gly Lys Glu Gln Val Ile Lys Ser Cys Val
    50                  55                  60

Ser Leu Pro Glu Leu Asn Ala Gln Val Phe Cys His Ser Ser Asn Asn
65                  70                  75                  80

Val Thr Lys Thr Glu Cys Cys Phe Thr Asp Phe Cys Asn Asn Ile Thr
                85                  90                  95

Leu His Leu Pro Thr Gly Leu Pro Leu Leu Val Gln Arg Thr Ile Ala
            100                 105                 110

Arg Thr Ile Val Leu Gln Glu Ile Val Gly Lys Gly Arg Phe Gly Glu
    115                 120                 125

Val Trp His Gly Arg Trp Cys Gly Glu Asp Val Ala Val Lys Ile Phe
130                 135                 140

Ser Ser Arg Asp Glu Arg Ser Trp Phe Arg Glu Ala Glu Ile Tyr Gln
145                 150                 155                 160

Thr Val Met Leu Arg His Glu Asn Ile Leu Gly Phe Ile Ala Ala Asp
                165                 170                 175
```

-continued

```
Asn Lys Asp Asn Gly Thr Trp Thr Gln Leu Trp Leu Val Ser Glu Tyr
            180                 185                 190

His Glu Gln Gly Ser Leu Tyr Asp Tyr Leu Asn Arg Asn Ile Val Thr
        195                 200                 205

Val Ala Gly Met Ile Lys Leu Ala Leu Ser Ile Ala Ser Gly Leu Ala
    210                 215                 220

His Leu His Met Glu Ile Val Gly Thr Gln Gly Lys Pro Ala Ile Ala
225                 230                 235                 240

His Arg Asp Ile Lys Ser Lys Asn Ile Leu Val Lys Cys Glu Thr
            245                 250                 255

Cys Ala Ile Ala Asp Leu Gly Leu Ala Val Lys His Asp Ser Ile Leu
            260                 265                 270

Asn Thr Ile Asp Ile Pro Gln Asn Pro Lys Val Gly Thr Lys Arg Tyr
        275                 280                 285

Met Ala Pro Glu Met Leu Asp Asp Thr Met Asn Val Asn Ile Phe Glu
    290                 295                 300

Ser Phe Lys Arg Ala Asp Ile Tyr Ser Val Gly Leu Val Tyr Trp Glu
305                 310                 315                 320

Ile Ala Arg Arg Cys Ser Val Gly Gly Ile Val Glu Glu Tyr Gln Leu
                325                 330                 335

Pro Tyr Tyr Asp Met Val Pro Ser Asp Pro Ser Ile Glu Glu Met Arg
            340                 345                 350

Lys Val Val Cys Asp Gln Lys Phe Arg Pro Ser Ile Pro Asn Gln Trp
        355                 360                 365

Gln Ser Cys Glu Ala Leu Arg Val Met Gly Arg Ile Met Arg Glu Cys
    370                 375                 380

Trp Tyr Ala Asn Gly Ala Ala Arg Leu Thr Ala Leu Arg Ile Lys Lys
385                 390                 395                 400

Thr Ile Ser Gln Leu Cys Val Lys Glu Asp Cys Lys Ala
                405                 410

<210> SEQ ID NO 5
<211> LENGTH: 1011
<212> TYPE: DNA
<213> ORGANISM: Homo sapiens
<220> FEATURE:
<221> NAME/KEY: CDS
<222> LOCATION: (1)...(1011)

<400> SEQUENCE: 5 atg acc cgg gcg ctc tgc tca gcg ctc cgc cag gct ctc ctg ctg ctc     48
Met Thr Arg Ala Leu Cys Ser Ala Leu Arg Gln Ala Leu Leu Leu Leu
1               5                   10                  15 gca gcg gcc gcc gag ctc tcg cca gga ctg aag tgt gta tgt ctt ttg     96
Ala Ala Ala Ala Glu Leu Ser Pro Gly Leu Lys Cys Val Cys Leu Leu
            20                  25                  30 tgt gat tct tca aac ttt acc tgc caa aca gaa gga gca tgt tgg gca    144
Cys Asp Ser Ser Asn Phe Thr Cys Gln Thr Glu Gly Ala Cys Trp Ala
        35                  40                  45 tca gtc atg cta acc aat gga aaa gag cag gtg atc aaa tcc tgt gtc    192
Ser Val Met Leu Thr Asn Gly Lys Glu Gln Val Ile Lys Ser Cys Val
    50                  55                  60 tcc ctt cca gaa ctg aat gct caa gtc ttc tgt cat agt tcc aac aat    240
Ser Leu Pro Glu Leu Asn Ala Gln Val Phe Cys His Ser Ser Asn Asn
65                  70                  75                  80 gtt acc aaa acc gaa tgc tgc ttc aca gat ttt tgc aac aac ata aca    288
Val Thr Lys Thr Glu Cys Cys Phe Thr Asp Phe Cys Asn Asn Ile Thr
                85                  90                  95
```

```
ctg cac ctt cca aca gat aat gga act tgg act caa ctt tgg ctg gta        336
Leu His Leu Pro Thr Asp Asn Gly Thr Trp Thr Gln Leu Trp Leu Val
        100                 105                 110 tct gaa tat cat gaa cag ggc tcc tta tat gac tat ttg aat aga aat        384
Ser Glu Tyr His Glu Gln Gly Ser Leu Tyr Asp Tyr Leu Asn Arg Asn
            115                 120                 125 ata gtg acc gtg gct gga atg atc aag ctg gcg ctc tca att gct agt        432
Ile Val Thr Val Ala Gly Met Ile Lys Leu Ala Leu Ser Ile Ala Ser
    130                 135                 140 ggt ctg gca cac ctt cat atg gag att gtt ggt aca caa ggt aaa cct        480
Gly Leu Ala His Leu His Met Glu Ile Val Gly Thr Gln Gly Lys Pro
145                 150                 155                 160 gct att gct cat cga gac ata aaa tca aag aat atc tta gtg aaa aag        528
Ala Ile Ala His Arg Asp Ile Lys Ser Lys Asn Ile Leu Val Lys Lys
                165                 170                 175 tgt gaa act tgt gcc ata gcg gac tta ggg ttg gct gtg aag cat gat        576
Cys Glu Thr Cys Ala Ile Ala Asp Leu Gly Leu Ala Val Lys His Asp
            180                 185                 190 tca ata ctg aac act atc gac ata cct cag aat cct aaa gtg gga acc        624
Ser Ile Leu Asn Thr Ile Asp Ile Pro Gln Asn Pro Lys Val Gly Thr
        195                 200                 205 aag agg tat atg gct cct gaa atg ctt gat gat aca atg aat gtg aat        672
Lys Arg Tyr Met Ala Pro Glu Met Leu Asp Asp Thr Met Asn Val Asn
    210                 215                 220 atc ttt gag tcc ttc aaa cga gct gac atc tat tct gtt ggt ctg gtt        720
Ile Phe Glu Ser Phe Lys Arg Ala Asp Ile Tyr Ser Val Gly Leu Val
225                 230                 235                 240 tac tgg gaa ata gcc cgg agg tgt tca gtc gga gga att gtt gag gag        768
Tyr Trp Glu Ile Ala Arg Arg Cys Ser Val Gly Gly Ile Val Glu Glu
                245                 250                 255 tac caa ttg cct tat tat gac atg gtg cct tca gat ccc tcg ata gag        816
Tyr Gln Leu Pro Tyr Tyr Asp Met Val Pro Ser Asp Pro Ser Ile Glu
            260                 265                 270 gaa atg aga aag gtt gtt tgt gac cag aag ttt cga cca agt atc cca        864
Glu Met Arg Lys Val Val Cys Asp Gln Lys Phe Arg Pro Ser Ile Pro
        275                 280                 285 aac cag tgg caa agt tgt gaa gca ctc cga gtc atg ggg aga ata atg        912
Asn Gln Trp Gln Ser Cys Glu Ala Leu Arg Val Met Gly Arg Ile Met
    290                 295                 300 cgt gag tgt tgg tat gcc aac gga gcg gcc cgc cta act gct ctt cgt        960
Arg Glu Cys Trp Tyr Ala Asn Gly Ala Ala Arg Leu Thr Ala Leu Arg
305                 310                 315                 320 att aag aag act ata tct caa ctt tgt gtc aaa gaa gac tgc aaa gcc       1008
Ile Lys Lys Thr Ile Ser Gln Leu Cys Val Lys Glu Asp Cys Lys Ala
                325                 330                 335 taa                                                                   1011
 *

<210> SEQ ID NO 6
<211> LENGTH: 336
<212> TYPE: PRT
<213> ORGANISM: Homo sapiens

<400> SEQUENCE: 6

Met Thr Arg Ala Leu Cys Ser Ala Leu Arg Gln Ala Leu Leu Leu Leu
1               5                   10                  15

Ala Ala Ala Ala Glu Leu Ser Pro Gly Leu Lys Cys Val Cys Leu Leu
            20                  25                  30

Cys Asp Ser Ser Asn Phe Thr Cys Gln Thr Glu Gly Ala Cys Trp Ala
        35                  40                  45
```

Ser Val Met Leu Thr Asn Gly Lys Glu Gln Val Ile Lys Ser Cys Val
            50                  55                  60

Ser Leu Pro Glu Leu Asn Ala Gln Val Phe Cys His Ser Ser Asn Asn
 65                  70                  75                  80

Val Thr Lys Thr Glu Cys Cys Phe Thr Asp Phe Cys Asn Asn Ile Thr
                 85                  90                  95

Leu His Leu Pro Thr Asp Asn Gly Thr Trp Thr Gln Leu Trp Leu Val
                100                 105                 110

Ser Glu Tyr His Glu Gln Gly Ser Leu Tyr Asp Tyr Leu Asn Arg Asn
                115                 120                 125

Ile Val Thr Val Ala Gly Met Ile Lys Leu Ala Leu Ser Ile Ala Ser
    130                 135                 140

Gly Leu Ala His Leu His Met Glu Ile Val Gly Thr Gln Gly Lys Pro
145                 150                 155                 160

Ala Ile Ala His Arg Asp Ile Lys Ser Lys Asn Ile Leu Val Lys Lys
                165                 170                 175

Cys Glu Thr Cys Ala Ile Ala Asp Leu Gly Leu Ala Val Lys His Asp
                180                 185                 190

Ser Ile Leu Asn Thr Ile Asp Ile Pro Gln Asn Pro Lys Val Gly Thr
                195                 200                 205

Lys Arg Tyr Met Ala Pro Glu Met Leu Asp Asp Thr Met Asn Val Asn
210                 215                 220

Ile Phe Glu Ser Phe Lys Arg Ala Asp Ile Tyr Ser Val Gly Leu Val
225                 230                 235                 240

Tyr Trp Glu Ile Ala Arg Arg Cys Ser Val Gly Gly Ile Val Glu Glu
                245                 250                 255

Tyr Gln Leu Pro Tyr Tyr Asp Met Val Pro Ser Asp Pro Ser Ile Glu
                260                 265                 270

Glu Met Arg Lys Val Val Cys Asp Gln Lys Phe Arg Pro Ser Ile Pro
                275                 280                 285

Asn Gln Trp Gln Ser Cys Glu Ala Leu Arg Val Met Gly Arg Ile Met
                290                 295                 300

Arg Glu Cys Trp Tyr Ala Asn Gly Ala Ala Arg Leu Thr Ala Leu Arg
305                 310                 315                 320

Ile Lys Lys Thr Ile Ser Gln Leu Cys Val Lys Glu Asp Cys Lys Ala
                325                 330                 335

<210> SEQ ID NO 7
<211> LENGTH: 75
<212> TYPE: PRT
<213> ORGANISM: Homo sapiens

<400> SEQUENCE: 7

Leu Lys Cys Val Cys Leu Leu Cys Asp Ser Ser Asn Phe Thr Cys Gln
  1               5                  10                  15

Thr Glu Gly Ala Cys Trp Ala Ser Val Met Leu Thr Asn Gly Lys Glu
                 20                  25                  30

Gln Val Ile Lys Ser Cys Val Ser Leu Pro Glu Leu Asn Ala Gln Val
             35                  40                  45

Phe Cys His Ser Ser Asn Asn Val Thr Lys Thr Glu Cys Cys Phe Thr
         50                  55                  60

Asp Phe Cys Asn Asn Ile Thr Leu His Leu Pro
 65                  70                  75

ALK7 AND MYOSTATIN INHIBITORS AND USES THEREOF

RELATED APPLICATIONS

This application claims the benefit of U.S. Provisional Application Ser. No. 60/549,352, filed Mar. 2, 2004. All the teachings of the above-referenced application is incorporated herein by reference.

BACKGROUND OF THE INVENTION

Myostatin, or growth/differentiation factor 8 (GDF-8), belongs to the transforming growth factor-β (TGF-β) superfamily (McPherron et al., Nature 387:83-90 (1997)). The human myostatin gene has been cloned (Nestor et al. Proc. Natl. Acad. Sci. 95:149438-43 (1998)), and it has been reported that myostatin immunoreactivity is detectable in human skeletal muscle in both type 1 and type 2 fibers. With respect to function, myostatin may play a role in negatively regulating the growth and development of skeletal muscle (Nestor et al., supra).

The first evidence that myostatin may play a key role in negatively regulating muscle development came from a study with myostatin knock-out mice (McPherron et al., Nature 387:83-90 (1997)). In the myostatin null mice, the animals were rather normal except that they were significantly larger than wild-type mice and had a large and widespread increase in skeletal muscle mass. Furthermore, it was also determined that two breeds of cattle, characterized by increased muscle mass, have mutations in the myostatin coding sequence (McPherron et al., Proc. Natl. Acad. Sci. 94:12457-61 (1997)). Additionally, it should be noted that the serum and intramuscular concentrations of immunoreactive myostatin are increased in HIV-infected men with muscle wasting compared with healthy men, and correlate inversely with the fat-free mass index. These data support the hypothesis that myostatin is a negative regulator of skeletal muscle growth in adult men and contributes to muscle wasting in HIV-infected men (Nestor et al., supra).

In view of the above findings, a need exists for a manner of regulating myostatin activity, particularly in individuals who experience muscle wasting as a result of a condition or disease state such as, for example, aging, Autoimmune Deficiency Syndrome (AIDS), Multiple Sclerosis, and cancer. The present invention provides methods and compositions which may be utilized to help individuals with such muscle wasting conditions and provides further insight into the regulation of myostatin gene expression.

SUMMARY OF THE INVENTION

One aspect of the invention provides pharmaceutical preparations for increasing muscle mass in vivo. Exemplary preparations of the subject invention include polypeptides including the ligand binding domain of ALK7. These so-called "ALK7 decoys" can be used to reduce the severity of a pathologic condition, which is characterized, at least in part, by an abnormal amount, development or metabolic activity of muscle or adipose tissue in a subject. For instance, the pharmaceutical preparations of the present invention can be administered in an amount effective to prevent, ameliorate or reduce the severity of a wasting disorder, such as cachexia, anorexia, DMD syndrome, BMD syndrome, AIDS wasting syndrome, muscular dystrophies, neuromuscular diseases, motor neuron diseases, diseases of the neuromuscular junction, and inflammatory myopathies. A pharmaceutical preparation may act by inhibiting myostatin-mediated signaling, by inhibiting ALK7-mediated signaling, or by a more complex mechanism.

Another aspect of the invention provides a pharmaceutical preparation for inhibiting myostatin. Exemplary preparations of the subject invention include a myostatin inhibitor that binds to myostatin in a manner that inhibits binding of an ALK7 receptor to myostatin. Preferably, the myostatin inhibitor binds to the "ALK7 epitope" (defined below) of myostatin.

In certain embodiments, a pharmaceutical preparation comprises an inhibitor that is a polypeptide that includes a ligand binding domain (e.g., myostatin, nodal, activin AB, or activin B binding domain) of an ALK7 receptor. For instance, the ligand binding domain can be derived from a human ALK7 protein, such shown in SEQ ID No. 2, such as amino acid residues

```
LKCVCLLCDSSNFTCQTEGACWASVMLTNGKEQVIKSCVSLPELNAQVF
CHSSNNVTKTECCFTDFCNNITLHLP
(residues 26-100 of SEQ ID No. 2).
```

In certain embodiments, the inhibitor includes a truncated extracellular domain from ALK7. In other embodiments, the inhibitor can be a soluble ALK7 splice variant, such as sALK7a (SEQ ID No. 4) or sALK7b (SEQ ID No. 6).

Also included are ALK7 derived variant sequence, e.g., ligand binding domains that retain ligand binding activity. Variant sequences may be desirable as a way to alter selectivity of the inhibitor (e.g., relative binding to myostatin, GDF11, activin or nodal binding), alter other binding characteristics with respect to myostatin or other ligand binding (such as $K_d$, and/or $K_{on}$ or $K_{off}$ rates), or improve biodistribution or half life in vivo or on the shelf.

In certain preferred embodiments, the myostatin binding domain binds myostatin with a $K_d$ of 1 μM or less, and more preferably a $K_d$ of 100 nM, 10 nM or even 1 nM or less.

In certain embodiments, the ligand binding domain is part of a fusion protein including, in addition to the ligand binding domain, one or more polypeptide portions that enhance one or more of in vivo stability, in vivo half life, uptake/administration, tissue localization or distribution, formation of protein complexes, and/or purification. For instance, the fusion protein can include an immunoglobulin Fc domain. In a preferred embodiment, the Fc domain is an IgG1 Fc fragment. An IgG1 Fc fragment may include various alterations, including, for example, mutations that reduce binding to Fcγ Receptor and mutations that decreased binding to MHC class I-related Fc-receptor (FcRN). Examples of mutations include mutations in the an Fc portion at positions 265 (Asp to Ala), 322 (Lys to Ala), and 434 (Asn to Ala). The fusion protein may include a purification subsequence, such as an epitope tag, a FLAG tag, a polyhistidine sequence, or as a GST fusion.

In certain embodiments, the ligand binding domain is part of a protein that includes one or more modified amino acid residues, such as a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent.

Based in part on the discovery that myostatin binds to ALK7, the present invention also contemplates the use of polypeptide affinity reagents that bind to myostatin and compete with the binding of an ALK7 receptor. For instance, such affinity reagents include antibody agents, as well as peptides and scaffolded peptides that bind to and inhibit myostatin.

Exemplary antibodies of the present invention include recombinant antibodies and monoclonal antibodies, as well as constructs derived from antigen binding fragments thereof, such as $V_H$ domains, $V_L$ domains, scFv's, Fab fragments, Fab' fragments, F(ab')$_2$ constructs, Fv's, and disulfide linked Fv's. In certain preferred embodiments, the antibody agent is a fully human antibody or a humanized chimeric antibody, or is an antigen binding fragment thereof.

In still other embodiments, a mysotatin inhibitor is a small organic molecule that selectively binds to myostatin and competes with the binding of an ALK7 receptor. Preferred inhibitors of this class are molecules having molecular weights less than 2500 amu, and even more preferably less than 2000, 1000 or even 750 amu.

In certain embodiments, a myostatin inhibitor is selective for binding and inhibition of myostatin, e.g., relative to GDF11 and/or nodal. For instance, the myostatin inhibitor can be one which has a dissociation constant ($K_d$) for myostatin binding that is at least 2 times less than its $K_d$ for binding GDF11 and/or nodal, and even more preferably at least 5, 10, 100 or even 1000 times less. Whether by virtue of binding kinetics or biodistribution, the subject myostatin inhibitor can also be selected based on relative in vivo potency, such as an inhibitor that has an $EC_{50}$ for inhibiting myostatin activity, or a particular physiological consequence (such as promoting muscle growth, promoting bone density or inducing adipocytes differentiation) that is at least 2 times less than its $EC_{50}$ for inhibiting GDF11 and/or nodal activities, and even more preferably at least 5, 10, 100 or even 1000 times less.

In certain preferred embodiments, the myostatin inhibitor binding domain binds myostatin with a $K_d$ of 1 μM or less, and more preferably a $K_d$ of 100 nM, 10 nM or even 1 nM or less.

In certain embodiments, the subject inhibitor preparations may be prepared so as to be suitable for use in a human patients. In preferred embodiments, the subject preparations of myostatin inhibitors will be substantially free of pyrogenic materials so as to be suitable for administration to a human patient.

In other embodiments, the subject inhibitors can be used to non-human animals, particularly other mammals. For example, the compounds of the present invention can be given to chickens, turkeys, livestock animals (such as sheep, pigs, horses, cattle, etc.), companion animals (e.g., cats and dogs) or may have utility in aquaculture to accelerate growth and improve the protein/fat ratio. To further illustrate, the subject inhibitors can be used to stimulate growth or enhance feed efficiency of animals raised for meat production to improve carcass quality, or to increase milk production in dairy cattle.

Another aspect of the invention relates to packaged pharmaceuticals comprising a pharmaceutical preparation of a myostatin inhibitor, as described herein, and a label or instructions for use in promoting growth of muscle tissue in a human patient.

Still another aspect of the invention relates to packaged pharmaceuticals comprising a pharmaceutical preparation of a myostatin inhibitor, as described herein, and a label or instructions for veterinarian use in promoting growth of muscle tissue in a non-human mammal.

Yet another aspect of the invention provides a pharmaceutical preparation suitable for use in a mammal, comprising: a vector including a coding sequence of a polypeptide inhibitor (such as an ALK7 decoy, an antibody agent, a peptide or a scaffolded peptide) that binds to an ALK7 receptor binding site on myostatin or other ALK7 ligands and inhibits signaling by myostatin or other ALK7 ligand, and transcriptional control sequences for causing expression of the polypeptide myostatin inhibitor in vivo in an amount effective for promoting growth of muscle tissue in the treated mammal. The preparation may include agents that enhance the uptake of the vector by cells of the treated mammal.

Another aspect of the invention relates to a method for inhibiting myostatin signal transduction in vivo by administering a pharmaceutical preparation of one or more of the myostatin inhibitors disclosed herein. The subject method can be used to promote muscle growth, promote adipogenic differentiation, and/or promote bone growth or mineralization in human patients or in non-human animals.

In certain embodiments, the treatment methods of the present invention can be used to reduce the severity of a pathologic condition, which is characterized, at least in part, by an abnormal amount, development or metabolic activity of muscle or adipose tissue in a subject. For instance, the pharmaceutical preparations of the present invention can be administered in an amount effective to prevent, ameliorate or reduce the severity of a wasting disorder, such as cachexia, anorexia, DMD syndrome, BMD syndrome, AIDS wasting syndrome, muscular dystrophies, neuromuscular diseases, motor neuron diseases, diseases of the neuromuscular junction, and inflammatory myopathies.

Exemplary muscular dystrophies that can be treated with a regimen including the subject myostatin include: Duchenne Muscular Dystrophy (DMD), Becker Muscular Dystrophy (BMD), Emery-Dreifuss Muscular Dystrophy (EDMD), Limb-Girdle Muscular Dystrophy (LGMD), Facioscapulohumeral Muscular Dystrophy (FSH or FSHD) (Also known as Landouzy-Dejerine), Myotonic Dystrophy (MMD) (Also known as Steinert's Disease), Oculopharyngeal Muscular Dystrophy (OPMD), Distal Muscular Dystrophy (DD), and Congenital Muscular Dystrophy (CMD).

Exemplary motor neuron diseases that can be treated with a regimen including the subject myostatin include: Amyotrophic Lateral Sclerosis (ALS) (Also known as Lou Gehrig's Disease), Infantile Progressive Spinal Muscular Atrophy (SMA, SMA1 or WH) (Also known as SMA Type 1, Werdnig-Hoffman), Intermediate Spinal Muscular Atrophy (SMA or SMA2) (Also known as SMA Type 2), Juvenile Spinal Muscular Atrophy (SMA, SMA3 or KW) (Also known as SMA Type 3, Kugelberg-Welander), Spinal Bulbar Muscular Atrophy (SBMA) (Also known as Kennedy's Disease and X-Linked SBMA), and Adult Spinal Muscular Atrophy (SMA).

Exemplary inflammatory myopathies that can be treated with a regimen including the subject myostatin include: Dermatomyositis (PM/DM), Polymyositis (PM/DM), and Inclusion Body Myositis (IBM).

Exemplary diseases of the neuromuscular junction that can be treated with a regimen including the subject myostatin include: Myasthenia Gravis (MG), Lambert-Eaton Syndrome (LES), and Congenital Myasthenic Syndrome (CMS).

Exemplary myopathies due to endocrine abnormalities that can be treated with a regimen including the subject myostatin include: Hyperthyroid Myopathy (HYPTM) and Hypothyroid Myopathy (HYPOTM).

Exemplary diseases of peripheral nerve that can be treated with a regimen including the subject myostatin include: Charcot-Marie-Tooth Disease (CMT), Dejerine-Sottas Disease (DS), and Friedreich's Ataxia (FA).

Other exemplary myopathies that can be treated with a regimen including the subject myostatin include: Myotonia Congenita (MC), Paramyotonia Congenita (PC), Central Core Disease (CCD), Nemaline Myopathy (NM), Myotubular Myopathy (MTM or MM), and Periodic Paralysis (PP).

Exemplary metabolic diseases of muscle that can be treated with a regimen including the subject myostatin include: Phosphorylase Deficiency (MPD or PYGM), Acid Maltase Deficiency (AMD), Phosphofructokinase Deficiency (PFKM), Debrancher Enzyme Deficiency (DBD), Mitochondrial Myopathy (MITO), Carnitine Deficiency (CD), Carnitine Palmityl Transferase Deficiency (CPT), Phosphoglycerate Kinase Deficiency (PGK), Phosphoglycerate Mutase Deficiency (PGAM or PGAMM), Lactate Dehydrogenase Deficiency (LDHA), and Myoadenylate Deaminase Deficiency (MAD)

The subject method can also be used to prevent, ameliorate or reduce the severity of a metabolic disorder, such as in the treatment of obesity or type II diabetes. To further illustrate, the subject inhibitor preparations can be used to decrease body fat proportion in a subject.

In still other embodiments, the inhibitor preparations can be used as part of such methods as: treating or preventing congestive heart failure; for reducing frailty associated with aging; increasing bone density (such as for treating osteoporosis) or accelerating bone fracture repair; treating growth retardation, treatment of physiological short stature, attenuating protein catabolic response such as after a major operation; reducing protein loss due to chronic illness; accelerating wound healing; accelerating the recovery of burn patients or patients having undergone major surgery; maintenance of skin thickness; metabolic homeostasis and renal homeostasis. Still other uses of the subject inhibitors include: treating growth hormone deficient adults and preventing catabolic side effects of glucocorticoids.

The subject pharmaceutical composition can also be used as myostatin antagonist to treat a number of neuronal system disease conditions, including CNS injuries/disease such as spinal cord injury and stroke, and PNS injuries/diseases.

The present invention also contemplates the use of the subject formulations conjointly with one or more other compounds useful in an effort to treat the diseases or therapeutic indications enumerated above. In these combinations, the therapeutic agents and the myostatin inhibitors of this invention may be independently and sequentially administered or co-administered. Combined therapy to inhibit bone resorption, prevent osteoporosis, reduce skeletal fracture, enhance the healing of bone fractures, stimulate bone formation and increase bone mineral density can be effectuated by combinations of bisphosphonates and the myostatin inhibitors of this invention. Bisphosphonates with these utilities include but are not limited to alendronate, tiludronate, dimethyl-APD, risedronate, etidronate, YM-175, clodronate, pamidronate, and BM-210995 (ibandronate).

The subject inhibitors may be combined with a mammalian estrogen agonist/antagonist. The term estrogen agonist/antagonist refers to compounds which bind with the estrogen receptor, inhibit bone turnover and prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue, and blocking the actions of estrogen in one or more tissues. A variety of these compounds are described and referenced below, however, other estrogen agonists/antagonists will be known to those skilled in the art. Exemplary estrogen agonist/antagonist include droloxifene and associated compounds (see U.S. Pat. No. 5,047,431), tamoxifen and associated compounds (see U.S. Pat. No. 4,536,516), 4-hydroxy tamoxifen (see U.S. Pat. No. 4,623,660), raloxifene and associated compounds (see 4U.S. Pat. No. 4,418,068), and idoxifene and associated compounds (see U.S. Pat. No. 4,839,155).

The subject inhibitors may also be combined with one or more of the following agents: glutamate antagonists (including partial antagonists) such as riluzole and topiramate; polypeptide growth factors, such as growth hormone (GH) and insulin-like growth factor 1 (IGF-1), or drugs that increases the body's own production of neurotrophic factors, such as xaliproden; anti-inflammatory agents, such as celecoxib (Celebrex) and other COX-2 inhibitors; antibiotics, such as minocycline (Minocin, Dynacin) or other agents that inhibit caspase enzymes; Protein kinase C inhibitors such as tamoxifen (Nolvadex); and various over-the-counter substances, including vitamin E, coenzyme Q10 and creatine.

BRIEF DESCRIPTION OF THE DRAWINGS

FIG. 2 shows results for the gastrocnemius muscle. FIG. 3 shows results for the quadriceps muscle. FIG. 4 shows results for the diaphragm muscle. In each case, a dosage of 3 mg/kg caused a statistically significant increase in muscle mass relative to control, and in the case of gastrocnemius and diaphragm muscles, the lower dosage of 1 mg/kg also caused statistically significant increase in muscle mass.

DETAILED DESCRIPTION OF THE INVENTION

I. Overview

Figure 1:
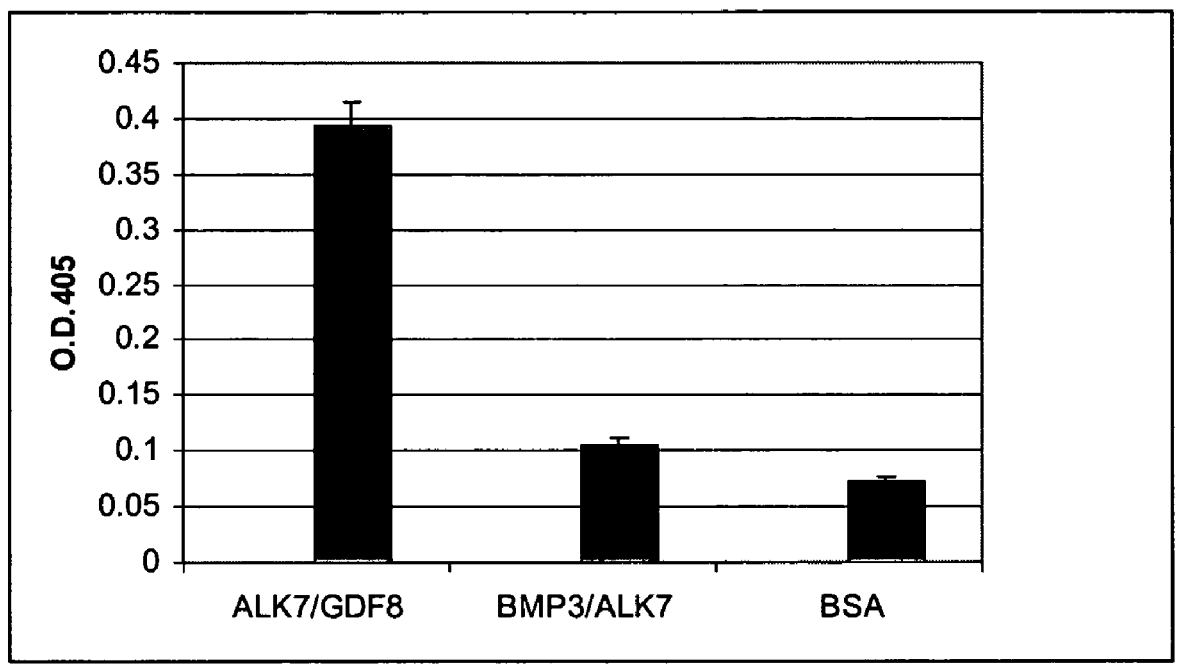
FIG. 1 shows the results of a sample binding assay demonstrating that ALK7 binds to GDF8 but not to a negative control, BMP3.

The disclosure relates in part to the discovery that myostatin (GDF-8) binds to the ALK7 receptor. The disclosure further relates to the discovery that administration of a soluble, ligand binding portion of the ALK7 receptor to a mammal causes an increase in muscle mass. It is well-known that, in a variety of mammals including humans, loss-of-function mutations in myostatin result in increased muscle mass. Schuelke M et al. N Engl J Med. 2004 Jun. 24;350(26):2682-8. McPherron A C, Lee S J, Proc Natl Acad Sci USA. 1997 Nov. 11;94(23):12457-61. Grobet L, et al. Nat Genet. 1997 September; 17(1):71-4. Accordingly, soluble ALK7 may increase muscle mass by binding to myostatin and inhibiting myostatin-mediated signaling. However, the precise mechanism of action may be substantially more complex. ALK7 is known to bind to Nodal, Activin AB, Activin B and, based on the results presented here, GDF11, a close homolog of GDF8. Tsuchida K, et al., Mol Cell Endocrinol. 2004 May 31;220 (1-2):59-65. Reissmann E, et al., Genes Dev. 2001 Aug. 1;15 (15):2010-22. It is likely that future studies will show that ALK7 binds to yet additional members of the TGF-β family. Therefore, soluble ALK7 may affect muscle mass in vivo by binding to and inhibiting the function of a plurality of signaling molecules. Nonetheless, the discovery that ALK7 binds to myostatin provides a host of agents that may be used to modulate myostatin activity by, for example, selectively disrupting myostatin-ALK7 interactions in vivo.

II. Definitions

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope an meaning of any use of a term will be apparent from the specific context in which the term is used.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values.

Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The methods of the invention may include steps of comparing sequences to each other, including wild-type sequence to one or more mutants/sequence variants Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, or "A") in the polymer sequence not containing the inserted or deleted residue.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity," in all its grammatical forms, refers to the degree of identity or correspondence between nucleic acid or amino acid sequences that may or may not share a common evolutionary origin.

However, in common usage and in the instant application, the term "homologous," when modified with an adverb such as "highly," may refer to sequence similarity and may or may not relate to a common evolutionary origin.

A nucleic acid molecule is "hybridizable" to another nucleic acid molecule, such as a cDNA, genomic DNA, or RNA, when a single stranded form of the nucleic acid molecule can anneal to the other micleic acid molecule under the appropriate conditions of temperature and solution ionic strength (see Sambrook et al. *Molecular Cloning: A Laboratory Manual*, Second Edition (1989) Cold Spring Harbor Laboratory Press, Cold Spring Harbor, N.Y.). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS).

Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC. SSC is 0.15 M NaCl, 0.015 M Na-citrate.

"High stringency condition" is well understood in the art to encompass conditions of hybridization which allow hybridization of structurally related, but not structurally dissimilar, nucleic acids. The term "stringent" is a term of art which is understood by the skilled artisan to describe any of a number of alternative hybridization and wash conditions which allow annealing of only highly complementary nucleic acids.

Exemplary high stringent hybridization conditions is equivalent to about 20-27° C. below the melting temperature ($T_m$) of the DNA duplex formed in about 1 M salt. Many equivalent procedures exist and several popular molecular cloning manuals describe suitable conditions for stringent hybridization and, furthermore, provide formulas for calculating the length of hybrids expected to be stable under these conditions (see e.g. *Current Protocols in Molecular Biology*, John Wiley & Sons, N.Y. (1989), 6.3.1-6 or 13.3.6; or pages 9.47-9.57 of Sambrook, et al. (1989) *Molecular Cloning, 2nd* ed., Cold Spring Harbor Press).

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$, for hybrids of nucleic acids having those sequences. The relative stability (corresponding to higher $T_m$) of micleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.51). For hybridization with shorter nucleic acids, i.e., oligonucleotides, the position of mismatches becomes more important, and the length of the oligonucleotide determines its specificity (see Sambrook et al., supra, 11.8). A minimum length for a hybridizable nucleic acid is at least about 10 nucleotides; preferably at least about 15 nucleotides; and more preferably the length is at least about 20 nucleotides.

Unless specified, the term "standard hybridization conditions" refers to a $T_m$ of about 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions.

Suitable hybridization conditions for oligonucleotides (e.g., for oligonucleotide probes or primers) are typically somewhat different than for full-length nucleic acids (e.g., full-length cDNA), because of the oligonucleotides' lower melting temperature. Because the melting temperature of oligonucleotides will depend on the length of the oligonucleotide sequences involved, suitable hybridization temperatures will vary depending upon the oligonucleotide molecules used. Exemplary temperatures may be 37° C. (for 14-base oligonucleotides), 48° C. (for 17-base oligonucleotides), 55° C. (for 20-base oligonucleotides) and 60° C. (for 23-base oligonucleotides). Exemplary suitable hybridization conditions for oligonucleotides include washing in 6×SSC, 0.05% sodium pyrophosphate, or other conditions that afford equivalent levels of hybridization.

"Polypeptide," "peptide" or "protein" are used interchangeably to describe a chain of amino acids that are linked together by chemical bonds called "peptide bonds." A protein or polypeptide, including an enzyme, may be a "native" or "wild-type," meaning that it occurs in nature; or it may be a "mutant," "variant," or "modified," meaning that it has been made, altered, derived, or is in some way different or changed from a native protein or from another mutant.

The term "ALK7 epitope" refers to the portion of myostatin to which the myostatin binding domain of ALK7 binds.

The terms "antibody" and "antibody agent" are used interchangeably herein, and refer to an immunoglobulin molecule obtained by in vitro or in vivo generation of the humoral response, and includes both polyclonal and monoclonal antibodies. The term also includes genetically engineered forms such as chimeric antibodies (e.g., humanized murine antibodies), heteroconjugate antibodies (e.g., bispecific antibodies), and recombinant single chain Fv fragments (scFv). The term "antibody" also includes antigen binding forms of antibodies (e.g., Fab', F(ab')$_2$, Fab, Fv, rIgG, and, inverted IgG). An antibody immunologically reactive with the ALK7 epitope can be generated in vivo or by recombinant methods such as selection of libraries of recombinant antibodies in phage or similar vectors. See, e.g., Huse et al. (1989) *Science* 246: 1275-1281; and Ward, et al. (1989) *Nature* 341:544-546; and Vaughan et al. (1996) *Nature Biotechnology*, 14:309-314

The term "antigen binding fragment" includes any portion of an antibody that binds to the ALK7 epitope. An antigen binding fragment may be, for example, a polypeptide including a CDR3 region, or other fragment of an immunoglobulin molecule which retains the affinity and specificity of the myostatin epitope.

"Specifically binds" includes reference to the preferential association of a ligand, in whole or part, with a particular target molecule (i.e., "binding partner" or "binding moiety") relative to compositions lacking that target molecule. It is, of course, recognized that a certain degree of non-specific interaction may occur between the subject myostatin neutralizing antibodies and a other proteins. Nevertheless, specific binding, may be distinguished as mediated through specific recognition of the myostatin protein. Typically specific binding results in a much stronger association between the antibody and myostatin protein than between the antibody and other proteins, e.g., GDF11. Specific binding by an antibody to myostatin under such conditions requires an antibody that is selected for its specificity for a particular protein. The affinity constant (Ka, as opposed to Kd) of the antibody binding site for its cognate monovalent antigen is at least $10^7$, usually at least $10^8$, preferably at least $10^9$, more preferably at least $10^{10}$, and most preferably at least $10^{11}$M. A variety of immunoassay formats are appropriate for selecting antibodies specifically reactive with myostatin. For example, solid-phase ELISA immunoassays are routinely used to select monoclonal antibodies specifically reactive with a protein. See Harlow and Lane (1988) Antibodies, A Laboratory Manual, Cold Spring Harbor Publications, New York, for a description of immunoassay formats and conditions that can be used to determine specific reactivity.

Immunoassays in the competitive binding format can be used to determine cross-reactivity of antibodies with myostatin, e.g., to identify whether a test antibody is a myostatin neutralizing antibody. For example, the myostatin protein, or the ALK7 epitope thereof is immobilized to a solid support. Test antibodies are added to the assay compete with the binding of ALK7 to the immobilized antigen. The ability of the test antibodies to compete with the binding of ALK7 to the immobilized myostatin antigen is compared.

Similarly, immunoassays in the competitive binding format can be used to determine cross-reactivity determinations, e.g., to determine the specificity of a myostatin neutralizing antibody. For example, the myostatin protein, or the myostatin epitope thereof is immobilized to a solid support. Epitopes from other proteins, such as GDF11 or other proteins having sequence homology with myostatin are added to the assay to compete with the binding of a potential myostatin neutralizing antibody to the immobilized antigen. The ability of the test peptides to compete with the binding of potential myostatin neutralizing antibody with the immobilized myostatin antigen is compared. The percent cross-reactivity of the potential myostatin neutralizing antibody for the other antigens is calculated, using standard calculations. In certain preferred embodiments, the subject myostatin neutralizing antibodies have less than 10% cross-reactivity with GDF11.

III. Exemplary Myostatin Inhibitors

A. ALK7 Decoys

In certain embodiments, the disclosure provides an inhibitor of a TGF-β mediated phemonenon that is a polypeptide that includes a ligand binding domain of an ALK7 receptor, such as a nodal binding domain, an activin AB or B binding domain, a GDF11 binding domain or, preferably, a myostatin binding domain. While it is expected that myostatin binding activity will be a particularly useful guide in identifying ALK7 portions and variants that are likely to have desirable effects in vivo, especially in increasing muscle mass, it is also expected that binding activity with respect to other ALK7 ligands may also be useful in identifying desirable ALK7 portions and variants. The full-length human ALK7 protein, SEQ ID No. 2, has 493 amino acids and exhibits all characteristics of TGFβ type I receptors, including an activin receptor-binding domain, a transmembrane domain, a GS domain, and a serine/threonine kinase domain. Preferred fragments of the human ALK7 protein are ones which lack the transmembrane domain, e.g., such as the extracellular domain of Met-1 through Leu-114 of SEQ ID No. 2 as well as fragments thereof that retain the ability to bind to and neutralize myostatin. For instance, the myostatin binding domain can be derived from the active receptor-binding domain of human ALK7 protein, such as amino acid residues

```
LKCVCLLCDSSNFTCQTEGACWASVMLTNGKEQVIKSCVSLPELNAQVF
CHSSNNVTKTECCFTDFCNNITLHLP
(residues 26-100 of SEQ ID No. 2).
```

In other embodiments, the inhibitor can be a soluble ALK7 splice variant, such as sALK7a (SEQ ID No. 4) or sALK7b (SEQ ID No. 6). Transcripts encoding the sALK7 isoforms differ from the full-length transcript by lacking exon III or both exons III and IV in sALK7a and sALK7b, respectively Also included are ALK7 derived variant sequence, e.g., myostatin or other ligand binding domains that retain myostatin, or other ligand, binding activity. Variant sequences may be desirable as a way to alter selectivity of the inhibitor (e.g., relative to GDF11 or nodal binding), alter other binding characteristics with respect to myostatin (such as $K_d$, and/or $K_{on}$ or $K_{off}$ rates), or improve biodistribution or half life in vivo or on the shelf.

Certain other ALK7 sequences are listed below, and the subject inhibitors can be derived from those proteins as well. These sequences are retrieved from public databases available on the internet. Additional homologs of the proteins in other species, especially mammals, can be readily obtained by standard molecular biology protocols, such as PCR, low stringency hybridization, Ab-mediated screening of expression libraries using antibodies cross-reacting with ALK7 homologs in target species, etc.

For example, sequence alignments using softwares such as DNAStar's MegaAlign (supra) can identify the most conserved regions in the known members of a protein family. PCR can then be carried out using degenerate oligoes covering such most conserved regions, and templates DNA from the target organism. In preferred embodiments, such conserved regions include the kinase domain, and/or the ligand binding domain.

These same conserved regions may be used to generate probes for screening nucleic acid libraries at moderate to low stringency hybridization conditions (see definition section).

ALK7 (Full-Length and Soluble Forms)

Various ALK7 receptors have been cloned, and their sequences deposited in public databases. The following tables lists ALK7 sequences found in public databases, using the human ALK7 sequence as a query in a BLAST search of the nr database at NCBI (National Center for Biotechnology Information).

| Species | Database Access No. | % identity/homology to Human Sequence |
|---|---|---|
| Human | NP_660302 | 100/100 |
| Rat | NP_620790 | 94/98 |
| Mouse | XP_194020 | 94/97 |
| Truncated human | AAP21993 | 99/99 |
| Soluble human ALK7a | AAP21994 | 99/99 |
| Soluble human ALK7b | AAP21995 | 99/100 |

* homologs with less than 90% identity to the human query sequence are not listed.

In certain embodiments, an effective ALK7 polypeptide comprises an amino acid sequence that is at least 90% identical to the sequence of amino acids 26-100 of SEQ ID NO: 2, and optionally at least 95%, 97%, 99% or 100% identical thereto. Preferably such variants retain binding activity with respect to at least one ALK7 ligand, particularly myostatin. Optionally, an ALK7 polypeptide comprises an amino acid sequence that is less than 100% identical to the sequence of amino acids 26-100 of SEQ ID NO: 2 but greater than 95%, 97%, or 99% identical thereto. Preferably such variants retain binding activity with respect to at least one ALK7 ligand, particularly myostatin.

B. Antibody Agents

The subject myostatin inhibitors may be generated in the form of antibodies that are immunoreactive with an epitope overlapping with the binding site of ALK7 (e.g., the "ALK7 epitope"), such that binding of the antibody would be competitive (including semi-competitive) with the binding of the ALK7 protein.

Immunoassays in the competitive binding format can be used to determine cross-reactivity of other antibodies with ALK7. For example, the myostatin protein, or a portion of which that binds ALK7, is immobilized to a solid support. Test antibodies are added to the assay. The ability of the test antibodies to compete with the binding of the ALK7 the immobilized myostatin antigen is compared.

Similarly, immunoassays in the competitive binding format can be used to determine cross-reactivity determinations, e.g., to determine the specificity of an antibody for myostatin. For example, the myostatin protein is immobilized to a solid support. Epitopes from other proteins, such as other related proteins such as nodal and GDF-11, are added to the assay. The ability of the test peptides or proteins to compete with the binding of the test antibody with the immobilized myostatin is compared. The percent cross-reactivity of the antibody for the other antigens, e.g., nodal or GDF-11, is calculated. In certain preferred embodiments, the subject antibodies have less than 10% cross-reactivity with nodal or GDF-11.

To illustrate the generation of myostatin neutralizing antibodies, it is noted using peptides based on the ALK7 epitope, anti-myostatin antisera or anti-myostatin monoclonal antibodies can be made using standard methods. A mammal such as a mouse, a hamster or rabbit can be immunized with an immunogenic form of the peptide (e.g., an antigenic fragment which is capable of eliciting an antibody response). Techniques for conferring immunogenicity on a protein or peptide include conjugation to carriers or other techniques well known in the art. For instance, a peptidyl portion of a myostatin protein including the ALK7 epitope can be administered in the presence of adjuvant. The progress of immunization can be monitored by detection of antibody titers in plasma or serum. Standard ELISA or other immunoassays can be used with the immunogen as antigen to assess the levels of antibodies.

Following immunization with a myostatin antigen, anti-myostatin antisera can be obtained and, if desired, polyclonal myostatin neutralizing antibodies isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature,* 256: 495-497), as the human B cell hybridoma technique (Kozbar et al., (1983) *Immunology Today,* 4: 72), and the EBV-hybridoma technique to produce human monoclonal antibodies (Cole et al., (1985) *Monoclonal Antibodies and Cancer Therapy*, Alan R. Liss, Inc. pp. 77-96). Hybridoma cells can be screened immunochemically for production of antibodies specifically reactive with myostatin and the monoclonal antibodies isolated. Synthetic antibodies, e.g., generated by combinatorial mutagenesis and phage display, are equivalents of antibodies generated by immunization.

The labeled antibody may be a polyclonal or monoclonal antibody. In one embodiment, the labeled antibody is a purified labeled antibody. The term "antibody" includes, for example, both naturally occurring and non-naturally occurring antibodies. Specifically, the term "antibody" includes polyclonal and monoclonal antibodies, and fragments thereof. Furthermore, the term "antibody" includes chimeric antibodies and wholly synthetic antibodies, and fragments thereof. The detectable marker may be, for example, selected, e.g., from a group consisting of radioisotopes, fluorescent compounds, enzymes, and enzyme co-factor. Methods of labeling antibodies are well known in the art.

Antibody fragments which contain the idiotype for the ALK7 epitope can be generated by known techniques. For example, such fragments include, but are not limited to: the $F(ab')_2$ fragments generated by pepsin digestion of the antibody molecule and the Fab fragments which can be generated by reducing disulfide bridges of the $F(ab')_2$ fragments.

One skilled in the art will appreciate that the invention also encompasses the use of antigen recognizing immunoglobulin fragments. Such immunoglobulin fragments include, for example, the Fab', $F(ab')_2$, Fv or Fab fragments, or other antigen recognizing immunoglobulin fragments. Such immunoglobulin fragments can be prepared, for example, by proteolytic enzyme digestion, for example, by pepsin or papain digestion, reductive alkylation, or recombinant techniques. The materials and methods for preparing immunoglobulin fragments are well known to those skilled in the art.

In addition, the immunoglobulin may be a single chain antibody ("SCA"). These can consist of single chain Fv fragments ("scFv") in which the variable light ("V[L]") and variable heavy ("V[H]") domains are linked by a peptide bridge or by disulfide bonds. Also, the immunoglobulin may consist of single V[H] domains (dAbs) which possess antigen-binding activity. See, e.g., Winter and Milstein, (1991) *Nature* 349:295; and Glockshaber et al., (1990) *Biochemistry* 29:1362.

Synthetic antibodies, e.g., generated by combinatorial mutagenesis and phage display, are equivalents of antibodies generated by immunization.

Another aspect of the present invention provides a cell which produces a polypeptide which includes an antigen binding fragment which bind to the ALK7 epitope of myostatin, e.g., with a Kd of $10^{-5}$M or less, and more preferably $10^{-6}$M, $10^{-7}$M, $10^{-8}$M, $10^{-9}$M or less. In preferred embodiments, the polypeptide is an antibody or fragment thereof.

C. Small Molecule Antagonists

In still other embodiments, the mysotatin inhibitor is a small organic molecule that selectively binds to myostatin and competes with the binding of an ALK7 receptor.

There are numerous approaches to screening for therapeutic agents that bind to myostatin and inhibit its productive binding to ALK7, e.g., prevent ALK7-mediated signal transduction.

A variety of assay formats will suffice and, in light of the present disclosure, those not expressly described herein will nevertheless be comprehended by one of ordinary skill in the art. Agents to be tested for their ability to act as inhibitors of ALK7-mediated myostatin activity can be produced, for example, by bacteria, yeast, plants or other organisms (e.g., natural products), produced chemically (e.g., small molecules, including peptidomimetics), or produced recombinantly. Test agents contemplated by the present invention include non-peptidyl organic molecules, peptides, polypeptides, peptidomimetics, sugars, hormones, and nucleic acid molecules (such as antisense or RNAi nucleic acid molecules). In a preferred embodiment, the test agent is a small organic molecule having a molecular weight of less than about 2,500 daltons.

The test agents can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity between myostatin and ALK7.

Merely to illustrate, in an exemplary screening assay of the present invention, the compound of interest is contacted with an isolated and purified myostatin polypeptide which is ordinarily capable of binding ALK7. To the mixture of the compound and myostatin polypeptide is then added a composition containing an ALK7 polypeptide. Detection and quantification of myostatin complexes provides a means for determining the compound's efficacy at inhibiting complex formation between the myostatin and ALK7 polypeptides. The efficacy of the compound can be assessed by generating dose response curves from data obtained using various concentrations of the test compound. Moreover, a control assay can also be performed to provide a baseline for comparison. In the control assay, isolated and purified ALK7 is added to a composition containing the myostatin polypeptide, and the formation of myostatin complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between the myostatin and ALK7 polypeptide and target polypeptide may be detected by a variety of techniques. For instance, modulation of the formation of complexes can be quantitated using, for example, detectably labeled proteins such as radiolabelled (e.g., $^{32}$P, $^{35}$S, $^{14}$C or $^{3}$H), fluorescently labeled (e.g., FITC), or enzymatically labelled myostatin or ALK7 polypeptides, by immunoassay, or by chromatographic detection.

In certain embodiments, it will be desirable to immobilize either the myostatin or the ALK7 polypeptide to facilitate separation of protein complexes from uncomplexed forms of one or both of the proteins, as well as to accommodate automation of the assay. Binding of the ALK7 polypeptide to myostatin, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/myostatin (GST/myostatin) fusion proteins can be adsorbed onto glutathione sepharose beads (Sigma Chemical, St. Louis, Mo.) or glutathione derivatized microtitre plates, which are then combined with the ALK7 polypeptide, e.g., an $^{35}$S-labeled ALK7 polypeptide, and the test compound, and the mixture incubated under conditions conducive to complex formation, e.g., at physiological conditions for salt and pH, though slightly more stringent conditions may be desired. Following incubation, the beads are washed to remove any unbound ALK7 polypeptide, and the matrix immobilized radiolabel determined directly (e.g., beads placed in scintilant), or in the supernatant after the protein complexes are subsequently dissociated. Alternatively, the complexes can be dissociated from the matrix, separated by SDS-PAGE, and the level of ALK7 polypeptide found in the bead fraction quantitated from the gel using standard electrophoretic techniques.

Other techniques for immobilizing proteins on matrices are also available for use in the subject assay. For instance, either of the myostatin or ALK7 polypeptides can be immobilized utilizing conjugation of biotin and streptavidin. For instance, biotinylated myostatin molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the myostatin but which do not interfere with ALK7 binding can be derivatized to the wells of the plate, and the myostatin trapped in the wells by antibody conjugation. As above, preparations of a ALK7 polypeptide and a test compound are incubated in the myostatin-presenting wells of the plate, and the amount of protein complex trapped in the well can be quantitated. Exemplary methods for detecting such complexes, in addition to those described above for the GST-immobilized complexes, include immunodetection of complexes using antibodies reactive with the ALK7 polypeptide, or which are reactive with the myostatin protein and compete for binding with the ALK7 polypeptide; as well as enzyme-linked assays which rely on detecting an enzymatic activity associated with the ALK7 polypeptide. In the instance of the latter, the enzyme can be chemically conjugated or provided as a fusion protein with a ALK7 polypeptide. To illustrate, the ALK7 polypeptide can be chemically cross-linked or genetically fused with horseradish peroxidase, and the amount of ALK7 polypeptide trapped in the complex can be assessed with a chromogenic substrate of the enzyme, e.g., 3,3'-diamino-benzadine terahydrochloride or 4-chloro-1-napthol. Likewise, a fusion protein comprising the ALK7 polypeptide and glutathione-S-transferase can be provided, and complex formation quantitated by detecting the GST activity using 1-chloro-2,4-dinitrobenzene (Habig et al (1974) *J Biol Chem* 249:7130).

In another embodiment, fluorescence polarization assays are used in the methods of the invention. To illustrate, an ALK7 polypeptide is conjugated to a small molecule fluorophore such as fluorescein or Oregon green. Binding of the tagged ALK7 polypeptide to a myostatin would cause a decrease in the mobility of the ALK7 polypeptide and thus, increase the polarization of the emitted light from the fluorophore. This technique thereby allows for measuring, either directly or indirectly, the degree of interaction between myostatin and an ALK7 polypeptide in the presence or absence of a test agent.

In another specific embodiment, fluorescence resonance energy transfer (FRET) assays are used in the methods of the invention. These assays utilize two fluorescently tagged species, where the emission spectrum of the shorter wavelength tag overlaps the excitation spectrum of the longer wavelength tag. Close proximity of the two molecules induced by binding allows nonradiative excitation of the long wavelength tag when the short wavelength tag is excited.

Furthermore, other modes of detection such as those based on optical waveguides (PCT Publication WO 96/26432 and U.S. Pat. No. 5,677,196), surface plasmon resonance (SPR), surface charge sensors, and surface force sensors are compatible with many embodiments of the invention.

Moreover, the subject polypeptides can be used to generate an interaction trap assay, also known as the "two hybrid assay," for identifying agents that disrupt or potentiate binding of myostatin to a ALK7. See for example, U.S. Pat. No. 5,283,317; Zervos et al. (1993) *Cell* 72:223-232; Madura et al. (1993) *J Biol Chem* 268:12046-12054; Bartel et al. (1993) *Biotechniques* 14:920-924; and Iwabuchi et al. (1993) *Oncogene* 8:1693-1696). In a specific embodiment, the present invention contemplates the use of reverse two hybrid systems to identify compounds (e.g., small molecules or peptides) that dissociate interactions between myostatin and an ALK7 polypeptide. See for example, Vidal and Legrain, (1999) *Nucleic Acids Res* 27:919-29; Vidal and Legrain, (1999) *Trends Biotechnol* 17:374-81; and U.S. Pat. Nos. 5,525,490; 5,955,280; 5,965,368.

IV. Exemplary Therapeutic Uses

The subject ALK7 soluble receptor and various myostatin inhibitors can be used in a number of therapeutic settings to treat a number of diseases resulting from or exacerbated by the presence of myostatin.

In certain embodiments, the subject inhibitors are used as part of a treatment for a muscular dystrophy. The term "muscular dystrophy" refers to a group of degenerative muscle diseases characterized by gradual weakening and deterioration of skeletal muscles and sometimes the heart and respiratory muscles. Muscular dystrophies are genetic disorders characterized by progressive muscle wasting and weakness that begin with microscopic changes in the muscle. As muscles degenerate over time, the person's muscle strength declines. Exemplary muscular dystrophies that can be treated with a regimen including the subject myostatin include: Duchenne Muscular Dystrophy (DMD), Becker Muscular Dystrophy (BMD), Emery-Dreifuss Muscular Dystrophy (EDMD), Limb-Girdle Muscular Dystrophy (LGMD), Facioscapulohumeral Muscular Dystrophy (FSH or FSHD) (Also known as Landouzy-Dejerine), Myotonic Dystrophy (MMD) (Also known as Steinert's Disease), Oculopharyngeal Muscular Dystrophy (OPMD), Distal Muscular Dystrophy (DD), Congenital Muscular Dystrophy (CMD).

Duchenne Muscular Dystrophy (DMD) was first described by the French neurologist Guillaume Benjamin Amand Duchenne in the 1860s. Becker Muscular Dystrophy (BMD) is named after the German doctor Peter Emil Becker, who first described this variant of DMD in the 1950s. DMD is one of the most frequent inherited diseases in males, affecting one in 3,500 boys. DMD occurs when the dystrophin gene, located on the short arm of the X chromosome, is broken. Since males only carry one copy of the X chromosome, they only have one copy of the dystrophin gene. Without the dystrophin protein, muscle is easily damaged during cycles of contraction and relaxation. While early in the disease muscle compensates by regeneration, later on muscle progenitor cells cannot keep up with the ongoing damage and healthy muscle is replaced by non-functional fibro-fatty tissue.

In DMD, boys begin to show signs of muscle weakness as early as age 3. The disease gradually weakens the skeletal or voluntary muscles, those in the arms, legs and trunk. By the early teens or even earlier, the boy's heart and respiratory muscles may also be affected. BMD is a much milder version of DMD. Its onset is usually in the teens or early adulthood, and the course is slower and far less predictable than that of DMD. (Though DMD and BMD affect boys almost exclusively, in rare cases they can affect girls.

Until the 1980s, little was known about the cause of any kind of muscular dystrophy. In 1986, the dystrophin gene deficiency was identified as the cause of DMD. BMD results from different mutations in the same gene. BMD patients have some dystrophin, but it's either insufficient in quantity or poor in quality. Having some dystrophin protects the muscles of those with BMD from degenerating as badly or as quickly as those of people with DMD.

Recent researches demonstrate that blocking or eliminating Myostatin function in vivo can effectively treat at least certain symptoms in DMD and BMD patients (Bogdanovich et al., supra; Wagner et al., supra). Thus, the subject ALK7 soluble receptor constitute an alternative means of blocking the function of Myostatin in vivo in DMD and BMD patients.

Similarly, the subject ALK7 soluble receptor provides an effective means to increase muscle mass in other disease conditions that are in need of muscle growth. For example, Gonzalez-Cadavid et al. (supra) reported that that Myostatin expression correlates inversely with fat-free mass in humans and that increased expression of the Myostatin gene is associated with weight loss in men with AIDS wasting syndrome. By inhibiting the function of Myostatin in AIDS patients, at least certain symptoms of AIDS may be alleviated, if not completely eliminated, thus significantly improving quality of life in AIDS patients.

Since loss of Myostatin function is also associated with fat loss without diminution of nutrient intake (Zimmers et al., supra; McPherron and Lee, supra), the subject ALK7 soluble receptors may further be used as a therapeutic agent for slowing or preventing the development of obesity and type II diabetes.

The cancer anorexia-cachexia syndrome is among the most debilitating and life-threatening aspects of cancer. Progressive weight loss in cancer anorexia-cachexia syndrome is a common feature of many types of cancer and is responsible not only for a poor quality of life and poor response to chemotherapy, but also a shorter survival time than is found in patients with comparable tumors without weight loss. Associated with anorexia, fat and muscle tissue wasting, psychological distress, and a lower quality of life, cachexia arises from a complex interaction between the cancer and the host. It is one of the most common causes of death among cancer patients and is present in 80% at death. It is a complex example of metabolic chaos effecting protein, carbohydrate, and fat metabolism. Tumors produce both direct and indirect abnormalities, resulting in anorexia and weight loss. Currently, there is no treatment to control or reverse the process.

Cancer anorexia-cachexia syndrome affects cytokine production, release of lipid-mobilizing and proteolysis-inducing factors, and alterations in intermediary metabolism. Although anorexia is common, a decreased food intake alone is unable to account for the changes in body composition seen in cancer patients, and increasing nutrient intake is unable to reverse the wasting syndrome. Cachexia should be suspected in patients with cancer if an involuntary weight loss of greater than five percent of premorbid weight occurs within a six-month period.

Since systemic overexpression of Myostatin in adult mice was found to induce profound muscle and fat loss analogous to that seen in human cachexia syndromes (Zimmers et al., supra), the subject ALK soluble receptor as a pharmaceutical composition can be beneficially used as a Myostatin antagonist/blocker to prevent, treat, or alleviate the symptoms of the cachexia syndrome, where muscle growth is desired.

In certain embodiments, the subject myostatin inhibitors, particularly ALK7-derived decoys, can be used to form pharmaceutical compositions that can be beneficially used to prevent, treat, or alleviate symptoms of a host of diseases involving neurodegeneration. While not wishing to be bound by any particular theory, the subject ALK7 receptors may antagonize the inhibitory feedback mechanism mediated through the wild-type ALK7 receptor, thus allowing new neuronal growth and differentiation. The subject ALK soluble receptor as a pharmaceutical composition can be beneficially used to prevent, treat, or alleviate symptoms of diseases with neurodegeneration, including Alzheimer's Disease (AD), Parkinson's Disease (PD), Amyotrophic Lateral Sclerosis (ALS), Huntington's disease, etc.

Alzheimer's disease (AD) is a chronic, incurable, and unstoppable central nervous system (CNS) disorder that occurs gradually, resulting in memory loss, unusual behavior, personality changes, and a decline in thinking abilities. These losses are related to the death of specific types of brain cells and the breakdown of connections between them.

AD has been described as childhood development in reverse. In most people with AD, symptoms appear after the age 60. The earliest symptoms include loss of recent memory, faulty judgment, and changes in personality. Later in the disease, those with AD may forget how to do simple tasks like washing their hands. Eventually people with AD lose all reasoning abilities and become dependent on other people for their everyday care. Finally, the disease becomes so debilitating that patients are bedridden and typically develop coexisting illnesses. AD patients most commonly die from pneumonia, 8 to 20 years from disease onset.

Parkinson's disease (PD) is a chronic, incurable, and unstoppable CNS disorder that occurs gradually and results in uncontrolled body movements, rigidity, tremor, and gait difficulties. These motor system problems are related to the death of brain cells in an area of the brain that produces dopamine—a chemical that helps control muscle activity.

In most people with PD, symptoms appear after age 50. The initial symptoms of PD are a pronounced tremor affecting the extremities, notably in the hands or lips. Subsequent characteristic symptoms of PD are stiffness or slowness of movement, a shuffling walk, stooped posture, and impaired balance. There are wide ranging secondary symptoms such as memory loss, dementia, depression, emotional changes, swallowing difficulties, abnormal speech, sexual dysfunction, and bladder and bowel problems. These symptoms will begin to interfere with routine activities, such as holding a fork or reading a newspaper. Finally, people with PD become so profoundly disabled that they are bedridden. People with PD usually die from pneumonia.

Amyotrophic lateral sclerosis (ALS; Lou Gehrig's disease; motor neuron disease) is a chronic, incurable, and unstoppable CNS disorder that attacks the motor neurons, components of the CNS that connect the brain to the skeletal muscles. In ALS, the motor neurons deteriorate and eventually die, and though a person's brain normally remains fully functioning and alert, the command to move never reaches the muscles.

Most people who get ALS are between 40 and 70 years old. The first motor neurons that weaken are those leading to the arms or legs. Those with ALS may have trouble walking, they may drop things, fall, slur their speech, and laugh or cry uncontrollably. Eventually the muscles in the limbs begin to atrophy from disuse. This muscle weakness will become debilitating and a person will need a wheel chair or become unable to function out of bed. Most ALS patients die from respiratory failure or from complications of ventilator assistance like pneumonia, 3-5 years from disease onset.

The causes of these neurological diseases has remained largely unknown. They are conventionally defined as distinct diseases, yet clearly show extraordinary similarities in basic processes and commonly demonstrate overlapping symptoms far greater than would be expected by chance alone. Current disease definitions fail to properly deal with the issue of overlap and a new classification of the neurodegenerative disorders has been called for.

Huntington's disease (HD) is another neurodegenerative disease resulting from genetically programmed degeneration of neurons in certain areas of the brain. This degeneration causes uncontrolled movements, loss of intellectual faculties, and emotional disturbance. HD is a familial disease, passed from parent to child through a dominant mutation in the wild-type gene. Some early symptoms of HD are mood swings, depression, irritability or trouble driving, learning new things, remembering a fact, or making a decision. As the disease progresses, concentration on intellectual tasks becomes increasingly difficult and the patient may have difficulty feeding himself or herself and swallowing. The rate of disease progression and the age of onset vary from person to person.

Tay-Sachs disease and Sandhoff disease are glycolipid storage diseases caused by the lack of lysosomal β-hexosaminidase (Gravel et al., in *The Metabolic Basis of Inherited Disease*, eds. Scriver et al., McGraw-Hill, New York, pp. 2839-2879, 1995). In both disorders, $G_{M2}$ ganglioside and related glycolipidssubstrates for β-hexosaminidaseaccumulate in the nervous system and trigger acute neurodegeneration. In the most severe forms, the onset of symptoms begins in early infancy. A precipitous neurodegenerative course then ensues, with affected infants exhibiting motor dysfunction, seizure, visual loss, and deafness. Death usually occurs by 2-5 years of age. Neuronal loss through an apoptotic mechanism has been demonstrated (Huang et al., *Hum. Mol. Genet.* 6: 1879-1885, 1997).

It is well-known that apoptosis plays a role in AIDS pathogenesis in the immune system. However, HIV-1 also induces neurological disease. Shi et al. (*J. Clin. Invest.* 98: 1979-1990, 1996) examined apoptosis induced by HIV-1 infection of the central nervous system (CNS) in an in vitro model and in brain tissue from AIDS patients, and found that HIV-1 infection of primary brain cultures induced apoptosis in neurons and astrocytes in vitro. Apoptosis of neurons and astrocytes was also detected in brain tissue from 10/11 AIDS patients, including 5/5 patients with HIV-1 dementia and 4/5 nondemented patients.

Neuronal loss is a also a salient feature of prion diseases, such as Creutzfeldt-Jakob disease in human, BSE in cattle (mad cow disease), Scrapie Disease in sheep and goats, and feline spongiform encephalopathy (FSE) in cats.

The subject ALK7 soluble receptors are also useful to prevent, treat, and alleviate symptoms of various PNS disorders, such as the ones described below. The PNS is composed of the nerves that lead to or branch off from the CNS. The peripheral nerves handle a diverse array of functions in the body, including sensory, motor, and autonomic functions. When an individual has a peripheral neuropathy, nerves of the PNS have been damaged. Nerve damage can arise from a number of causes, such as disease, physical injury, poisoning, or malnutrition. These agents may affect either afferent or efferent nerves. Depending on the cause of damage, the nerve cell axon, its protective myelin sheath, or both may be injured or destroyed.

The term peripheral neuropathy encompasses a wide range of disorders in which the nerves outside of the brain and spinal cord—peripheral nerves—have been damaged. Peripheral neuropathy may also be referred to as peripheral neuritis, or if many nerves are involved, the terms polyneuropathy or polyneuritis may be used.

Peripheral neuropathy is a widespread disorder, and there are many underlying causes. Some of these causes are common, such as diabetes, and others are extremely rare, such as acrylamide poisoning and certain inherited disorders. The most common worldwide cause of peripheral neuropathy is leprosy. Leprosy is caused by the bacterium *Mycobacterium leprae*, which attacks the peripheral nerves of affected people. According to statistics gathered by the World Health Organization, an estimated 1.15 million people have leprosy worldwide.

Leprosy is extremely rare in the United States, where diabetes is the most commonly known cause of peripheral neuropathy. It has been estimated that more than 17 million people in the United States and Europe have diabetes-related polyneuropathy. Many neuropathies are idiopathic—no known cause can be found. The most common of the inherited peripheral neuropathies in the United States is Charcot-Marie-Tooth disease, which affects approximately 125,000 persons.

Another of the better known peripheral neuropathies is Guillain-Barré syndrome, which arises from complications associated with viral illnesses, such as cytomegalovirus, Epstein-Barr virus, and human immunodeficiency virus (HIV), or bacterial infection, including Campylobacter jejuni and Lyme disease. The worldwide incidence rate is approximately 1.7 cases per 100,000 people annually. Other well-known causes of peripheral neuropathies include chronic alcoholism, infection of the varicella-zoster virus, botulism, and poliomyelitis. Peripheral neuropathy may develop as a primary symptom, or it may be due to another disease. For example, peripheral neuropathy is only one symptom of diseases such as amyloid neuropathy, certain cancers, or inherited neurologic disorders. Such diseases may affect the peripheral nervous system (PNS) and the central nervous system (CNS), as well as other body tissues.

Other PNS diseases treatable with the subject ALK7 soluble receptors include: *Brachial Plexus Neuropathies* (Diseases of the cervical and first thoracic roots, nerve trunks, cords, and peripheral nerve components of the brachial plexus. Clinical manifestations include regional pain, paresthesia; muscle weakness, and decreased sensation in the upper extremity. These disorders may be associated with trauma, including birth injuries; thoracic outlet syndrome; neoplasms, neuritis, radiotherapy; and other conditions. See Adams et al., Principles of Neurology, $6^{th}$ ed, pp 1351-2); *Diabetic Neuropathies* (Peripheral, autonomic, and cranial nerve disorders that are associated with disbetes mellitus. These conditions usually result from diabetic microvascular injury involving small blood vessels that supply nerves (vasa nervorum). Relatively common conditions which may be associated with diabetic neuropathy include third nerve palsy; mononeuropathy; mononeuropathy multiplex; diabetic amyotrophy; a painful polyneuropathy; autonomic neuropathy; and thoracoabdominal neuropathy. See Adams et al., Principles of Neurology, $6^{th}$ ed, p 1325); *Mononeuropathies* (Disease or trauma involving a single peripheral nerve in isolation, or out of proportion to evidence of diffuse peripheral nerve dysfunction. Mononeuropathy multiplex refers to a condition characterized by multiple isolated nerve injuries. Mononeuropathies may result from a wide variety of causes, including ischemia; traumatic injury; compression; connective tissue diseases; cumulative trauma disorders; and other conditions); *Neuralgia* (Intense or aching pain that occurs along the course or distribution of a peripheral or cranial nerve); *Peripheral Nervous System Neoplasms* (Neoplasms which arise from peripheral nerve tissue. This includes neurofibromas; Schwannomas; granular cell tumors; and malignant peripheral nerve sheath tumors. See DeVita Jr et al., Cancer: Principles and Practice of Oncology, $5^{th}$ ed, pp 1750-1); *Nerve Compression Syndromes* (Mechanical compression of nerves or nerve roots from internal or external causes. These may result in a conduction block to nerve impulses, due to, for example, myelin sheath dysfunction, or axonal loss. The nerve and nerve sheath injuries may be caused by ischemia; inflammation; or a direct mechanical effect); *Neuritis* (A general term indicating inflammation of a peripheral or cranial nerve. Clinical manifestation may include pain; paresthesias; paresis; or hyperthesia); *Polyneuropathies* (Diseases of multiple peripheral nerves. The various forms are categorized by the type of nerve affected (e.g., sensory, motor, or autonomic), by the distribution of nerve injury (e.g., distal vs. proximal), by nerve component primarily affected (e.g., demyelinating vs. axonal), by etiology, or by pattern of inheritance).

V. Exemplary Formulations

The subject compositions may be used alone, or as part of a conjoint therapy with other compounds/pharmaceutical compositions.

The soluble ALK7 receptor therapeutics for use in the subject methods may be conveniently formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the phosphopeptide therapeutics, its use in the pharmaceutical preparation of the invention is contemplated. Suitable vehicles and their formulation inclusive of other proteins are described, for example, in the book *Remington's Pharmaceutical Sciences* (*Remington's Pharmaceutical Sciences*. Mack Publishing Co., Easton, Pa., USA 1985). These vehicles include injectable "deposit formulations."

Pharmaceutical formulations of the present invention can also include veterinary compositions, e.g., pharmaceutical preparations of the ALK7 soluble receptor therapeutics suitable for veterinary uses, e.g., for the treatment of live stock (cow, sheep, goat, pig, and horse, etc.) or domestic animals, e.g., cats and dogs.

Methods of invention may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a therapeutic at a particular target site.

The pharmaceutical compositions according to the present invention may be administered as either a single dose or in multiple doses. The pharmaceutical compositions of the present invention may be administered either as individual therapeutic agents or in combination with other therapeutic agents. The treatments of the present invention may be combined with conventional therapies, which may be administered sequentially or simultaneously. The pharmaceutical compositions of the present invention may be administered by any means that enables the soluble ALK7 to reach the targeted cells/tissues/organs. In some embodiments, routes of administration include those selected from the group consisting of oral, intravesically, intravenous, intraarterial, intraperitoneal, local administration into the blood supply of the organ in which the targeted cells reside or directly into the cells. Intravenous administration is the preferred mode of administration. It may be accomplished with the aid of an infusion pump.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, intravesically, nasally, as by, for example, a spray, rectally, intravaginally, parenterally, intracistemally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular phosphopeptide therapeutic employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

The term "treatment" is intended to encompass also prophylaxis, therapy and cure.

The patient receiving this treatment is any animal in need, including primates, in particular humans, and other non-human mammals such as equines, cattle, swine and sheep; and poultry and pets in general.

The compound of the invention can be administered as such or in admixtures with pharmaceutically acceptable carriers and can also be administered in conjunction with other antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

Combined with certain formulations, the subject ALK7 receptor can be effective soluble agents. The phosphopeptide can be provided a fusion peptide along with a second peptide which promotes solubility. To illustrate, the ALK7 receptor of the present invention can be provided as part of a fusion polypeptide with all or a fragment of the hinge or Fc portion of the immunoglobulin, which can promote solubility and/or serum stability.

The present invention also contemplates a peptidomimetic sequence of the subject ALK7 soluble receptor as described herein.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" ($8^{th}$ Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

EXAMPLES

Example 1

ALK7 Binds to GDF8

A series of experiments were conducted to investigate the possibility that GDF8 binds to ALK7. ALK7-Fc chimera (5 ug/ml) was coated on plate overnight at 4° C. It was blocked with BSA for 2-3 hours at room temperature. Plates were washed with PBS plus 0.05% Tween20. Then the ligands (GDF8 or BMP3) were added to each well. Plates were incubated for 2 hours at room temperature. Plates were washed and binding was detected with biotinylated secondary antibody complexed with streptavidin alkaline phosphatase. Sample data from a representative experiment is shown in FIG. 1. The data show ALK7 binding to GDF8 but no significant binding to BMP3.

Example 2

Administration of Soluble ALK7 Increases Muscle Mass in Vivo

Male CB-17 SCID mice (6 week old; weight 20-25 g) were administered either ALK7-Fc (dose in Table 1) or phosphate buffered saline (PBS) control by intraperitoneal (IP) injection. Each animal received a total of five (5) injections, occurring on study days 0, 4, 8, 15 and 22 for all mice. Individual animal weights were taken once per week. Mice were monitored daily for signs of toxicity and morbidity. All mice were euthanized on twenty-eight (28) days after initiation of Test or Control Article Administration. Mice were euthanized by carbon dioxide inhalation and the Gastrocnemius, femoris rectus (quadriceps) and diaphragm muscles were dissected and weighed. The data was analyzed using Excel.

TABLE 1

| Study Treatment Groups: | | | |
| --- | --- | --- | --- |
| Group Number | Treatment | Concentration | Route |
| 1 | PBS | Buffer solution | IP |
| 2 | ALK-7Fc | 1 mg/kg | IP |
| 3 | ALK-7Fc | 3 mg/kg | IP |

Figure 2:
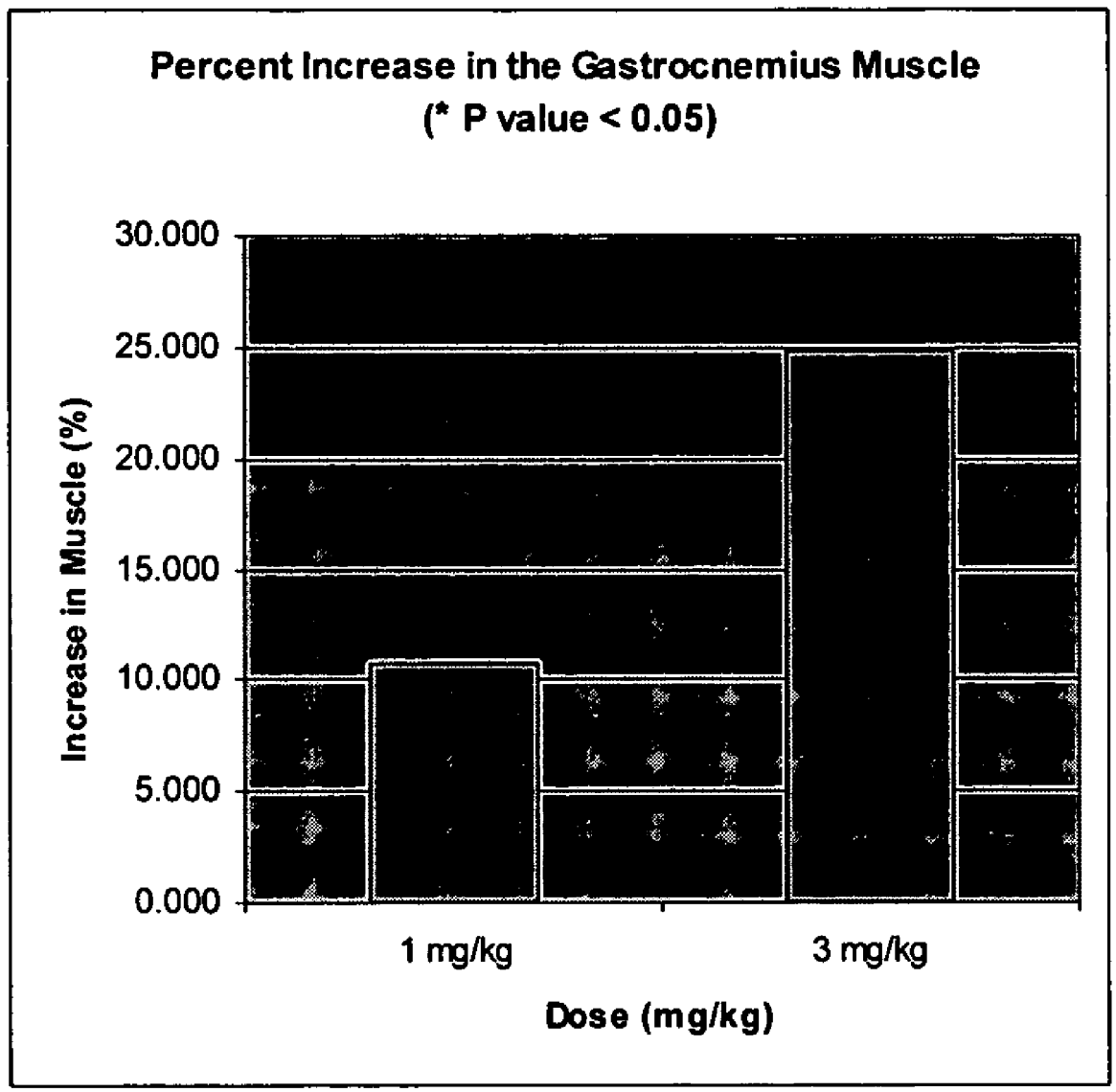
FIGS. 2-4 show the increase in muscle mass in mice treated with varying dosages of an ALK7-Fc fusion protein after a period of 28 days.
Figure 3:
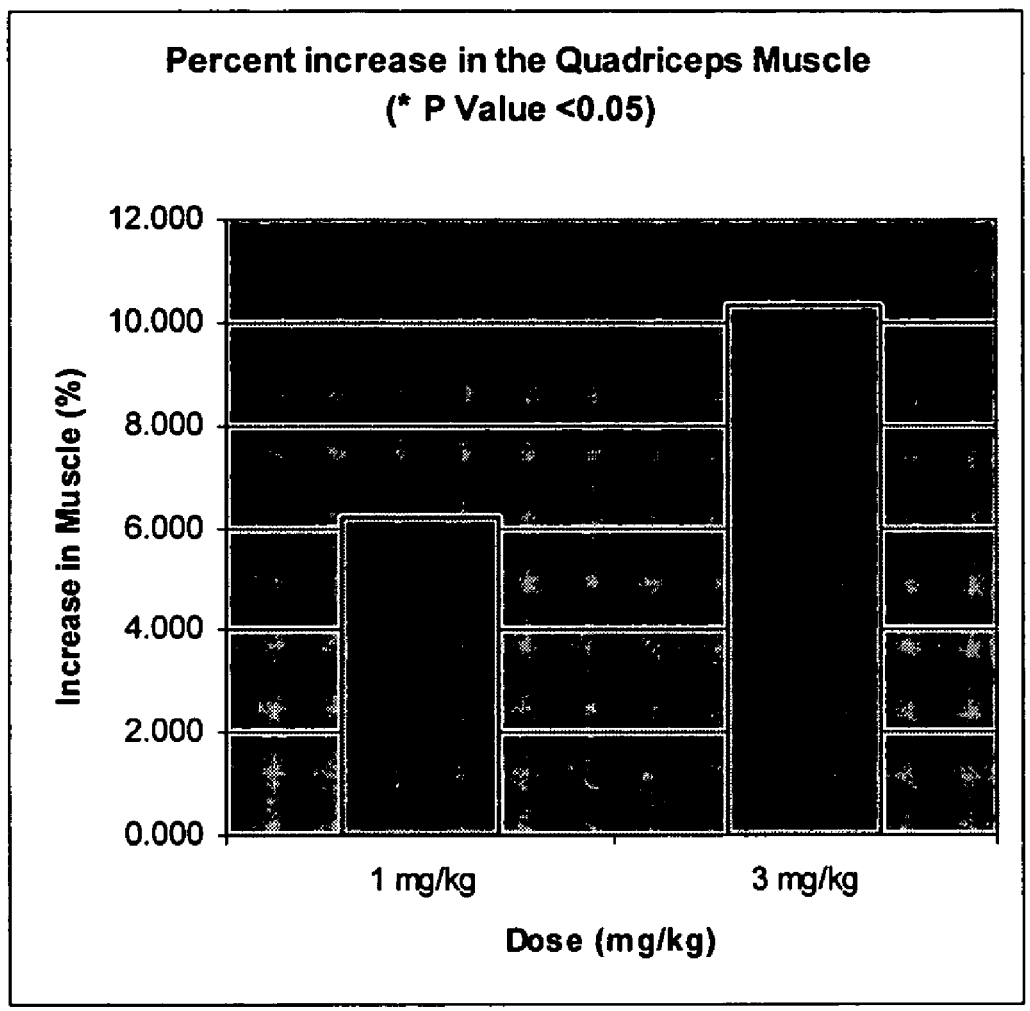
Figure 4:
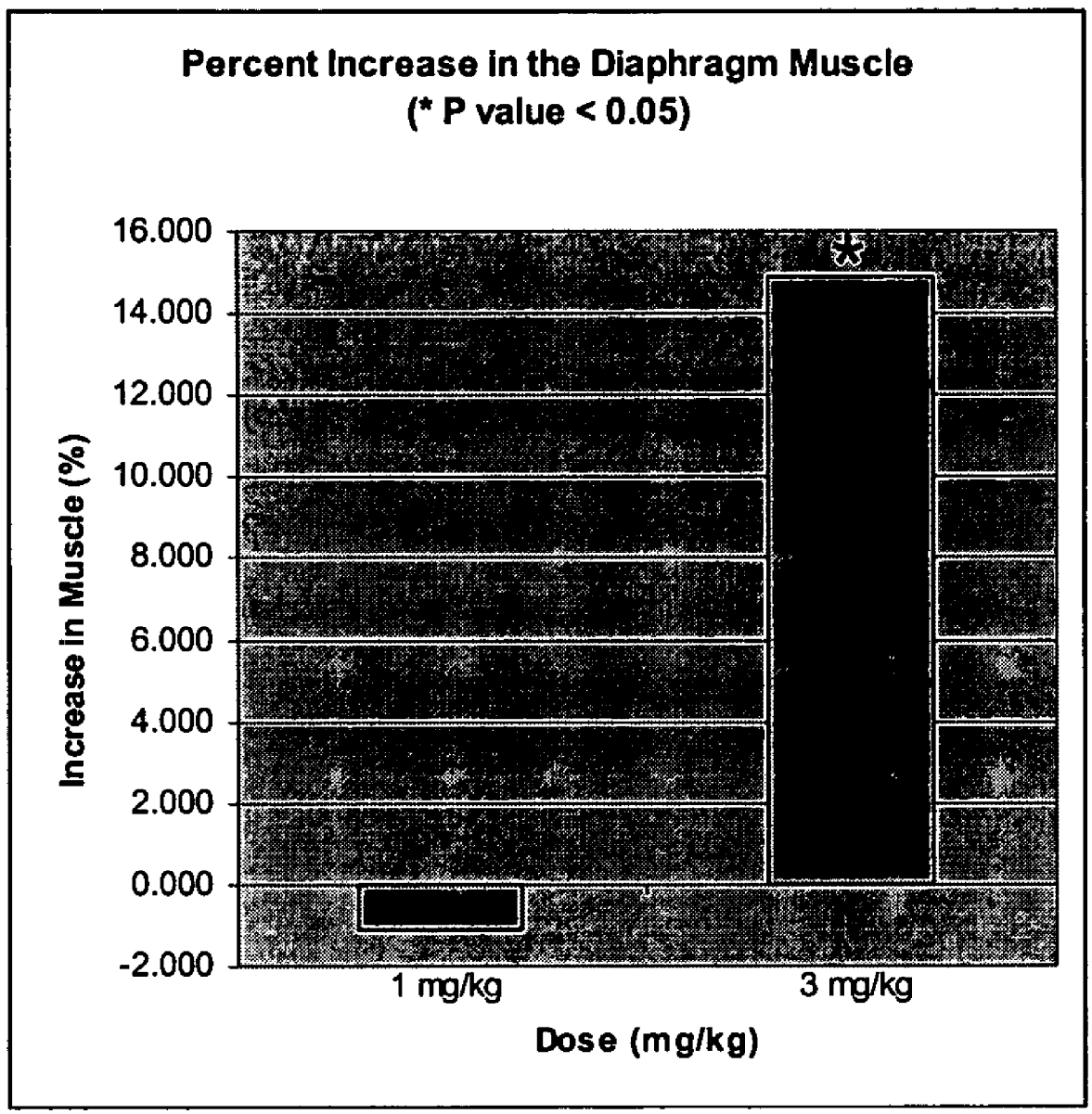

Results are shown in FIGS. 2-4. FIG. 2 shows results for the gastrocnemius muscle. FIG. 3 shows results for the quadriceps muscle. FIG. 4 shows results for the diaphragm muscle. In each case, a dosage of 3 mg/kg caused a statistically significant increase in muscle mass relative to control, and in the case of gastrocnemius and diaphragm muscles, the lower dosage of 1 mg/kg also caused statistically significant increase in muscle mass.

EQUIVALENTS

A skilled artisan will recognize, or be able to ascertain using no more than routine experimentation, many equivalents to the specific embodiments of the invention described herein. Such equivalents are intended to be encompassed by the following claims

We claim:

1. A pharmaceutical preparation for inhibiting myostatin, comprising a myostatin inhibitor that binds to myostatin in a manner that inhibits binding of an ALK7 receptor to myostatin, which preparation is substantially free of pyrogenic materials so as to be suitable for administration to a mammal, wherein the myostatin inhibitor is a fusion protein comprising i) a ligand binding domain of an ALK7 receptor which binds selectively to myostatin relative to BMP3 and competes with the binding of an ALK7 receptor and ii) an immunoglobulin Fc domain.

2. The preparation of claim 1, wherein said fusion protein comprises an amino acid sequence that is at least 95% identical to the amino acid sequence of SEQ ID NO: 2.

3. The preparation of claim 1, wherein said fusion protein comprises amino acid residues 26-100 of SEQ ID NO: 2.

4. The preparation of claim 1, wherein said fusion protein promotes muscle growth in a mammal when administered to said mammal.

* * * * *